US006333337B1

(12) United States Patent
Gross et al.

(10) Patent No.: US 6,333,337 B1
(45) Date of Patent: Dec. 25, 2001

(54) POTASSIUM CHANNEL INHIBITORS

(75) Inventors: Michael F. Gross, Durham; Neil A. Castle, Cary, both of NC (US)

(73) Assignee: ICAgen, Inc., Durham, NC (US)

( * ) Notice: Subject to any disclaimer, the term of this patent is extended or adjusted under 35 U.S.C. 154(b) by 0 days.

(21) Appl. No.: 09/229,315

(22) Filed: Jan. 13, 1999

Related U.S. Application Data

(60) Provisional application No. 60/072,719, filed on Jan. 27, 1998.

(51) Int. Cl.$^7$ .......... A61K 31/17; A61K 31/18; A61K 31/216; A61K 31/4155
(52) U.S. Cl. .......... 514/307; 514/311; 514/319; 514/355; 514/357; 514/455; 514/448; 514/466; 514/524; 514/602; 514/603; 514/821; 546/146; 546/166; 546/206; 546/293; 549/65; 549/72; 549/436; 558/413; 564/84; 564/85; 564/86; 564/87; 564/88; 564/89
(58) Field of Search .......... 564/84, 85, 86, 564/87, 88, 89; 514/602, 603, 821, 307, 311, 319, 355, 357, 455, 448, 466, 524; 546/146, 166, 206, 293; 549/65, 72, 436; 558/413

(56) References Cited

U.S. PATENT DOCUMENTS

| | | | |
|---|---|---|---|
| 3,953,506 | 4/1976 | Spicer et al. | 260/553 A |
| 4,005,140 | 1/1977 | Spicer et al. | 260/553 A |
| 4,975,453 | 12/1990 | Becker et al. | 514/456 |
| 5,006,512 | 4/1991 | Ohnishi | 514/21 |
| 5,215,985 | 6/1993 | Murphy et al. | 514/212 |
| 5,234,947 | 8/1993 | Cherksey | 514/449 |
| 5,242,947 | 9/1993 | Cherksey et al. | 514/628 |
| 5,310,932 | 5/1994 | Atwal et al. | 548/454 |
| 5,328,830 | 7/1994 | Janis et al. | 435/7.21 |
| 5,356,775 | 10/1994 | Herbert et al. | 435/6 |
| 5,401,758 | 3/1995 | Atwal et al. | 514/353 |
| 5,401,848 | 3/1995 | Atwal | 546/153 |
| 5,451,580 | 9/1995 | Murphy et al. | 514/212 |
| 5,453,421 | 9/1995 | Atwal et al. | 514/100 |
| 5,486,515 | 1/1996 | Brown et al. | 514/229.8 |
| 5,631,275 | 5/1997 | Englert et al. | 514/423 |
| 6,083,986 | 7/2000 | Castle et al. | |

FOREIGN PATENT DOCUMENTS

| | | |
|---|---|---|
| 0 317 321 | 5/1989 | (EP) . |
| 0 321 175 | 8/1989 | (EP) . |
| 0 472053 | 2/1992 | (EP) . |
| 0 488 616 | 6/1992 | (EP) . |
| 0 587 180 | 3/1994 | (EP) . |
| 0 608 858 | 8/1994 | (EP) . |
| 0 286 278 | 10/1998 | (EP) . |
| 1 479 544 | 7/1977 | (GB) . |
| 95/26342 | 10/1995 | (WO) . |
| 96/21640 | 7/1996 | (WO) . |
| 96/36596 | 11/1996 | (WO) . |
| 97/25893 | 7/1997 | (WO) . |
| 97/25983 | 7/1997 | (WO) . |
| 97/26300 | 7/1997 | (WO) . |
| 98/04521 | 2/1998 | (WO) . |
| 98/36749 | 8/1998 | (WO) . |

OTHER PUBLICATIONS

Still, et al., "Rapid Chromatographic Technique for Preparative Separation with Moderate Resolution," J. Org. Chem., vol. 43, No. 14, 1978, 2923–2925.
Castle, et al., "Characterization of 4–Aminopyridne Block of the Transient Outward $K^+$ Current in Adult Rat Ventricular Myocytes," The Journal of Pharmacology And Experimental, vol. 264, No. 3, 1450–1459, (No date).
Deal, et al., "Molecular Physiology of Cardiac Potassium Channels," Physiological Reviews, vol. 76, No. 1, Jan. 1996, 49–67.
Wang, et al., "Sustained Depolarization–Induced Outward Current in Human Atrial Myocytes, Evidence for a Novel Delayed Rectified $K^+$ Current Similar to Kv1.5 Cloned Channel Current," Circulation Research, vol. 73, No. 6, Dec. 1993, 1061–1076.
Hamill, "Improved Patch–Clamp Techniques for High–Resolution Current Recording from Cells and Cell–Free Membrane Patches," Pflüger Archiv, (1981) 391:85–100.
Fedida, et al., "Identity of a Novel Delayed Rectifier Current From Human Heart With a Cloned $K^+$ Channel Current," Circulation Research, vol. 73, No. 1, Jul. 1993, 210–216.
Chandy, et al., "Voltage–Gated Potassium Channels Are Required For Human T. Lymphocyte Activation," J. Exp. Med., vol. 160, Aug. 1984, 369–385.
Sanguinetti, "Modulation of Potassium Channels by Antiarrhythmic and Antihypertensive Drugs," Hypertension, vol. 19, No. E, Mar. 1992, 228–236.
Lynch, et al., "Therapeutic Potential of modulating Potassium Currents in the Diseased Myocardium," The FASEB Journal, vol. 6, Aug. 1992, 2952–2960.
Colatsky, et al, "Channel Specificity in Antiarrhythmic Drug Action," Circulation, vol. 82, No. 6, Dec. 1990, 2235–2242.
Halliwell, "$K^+$ Channels in the Central Nervous System," 348–381.
Amos, et al. "Differences Between Outward Currents of Human Atrial and Subepicardial Ventricular Myocytes," Journal of Physiology, (1986), 491.1, 31–50.
Wang, et al., "Effects of Flecanide, Quinidine, and 4–Aminopyridine on Transient Outward and Ultrarapid Delayed Rectifier Currents in Human Atrial Myocytes," The Journal of Pharmacology and Experimental Therapeutics, vol. 272, No. 1, 184–196, (No date).
Lin, et al., "Voltage–gated Potassium Channel Regulate Calcium–dependent Pathways Involved in Human T Lymphocyte Activation," J. Exp. Med., vol. 177, 637–645, (No date).

(List continued on next page.)

Primary Examiner—Peter O'Sullivan
(74) Attorney, Agent, or Firm—Banner & Witcoff, Ltd.

(57) ABSTRACT

Compounds useful as potassium channel inhibitors and especially useful for the treatment of cardiac arrhythmias and cell proliferative disorders are described.

42 Claims, No Drawings

OTHER PUBLICATIONS

Kaczorowki, et al., "lymphocyte Ion Channels as a Target for Immunosuppression," Perspective in Drug Discovery and Design 2 (1994) 233–248.

Leonard, et al., Selective Blockers of voltage–Gated $K^+$ Channels Depolarize Human T Lymphocytes: Mechanism of the Antiproliferative Effect of Charybdotoxin, vol. 89, 10094–10098, Nov. 1992.

Doupnik, et al., "The Inward Rectifier Potassium Channel Family," Current Opinion in Neurobiology, 1995, 5:268–277.

Chandy, et al., "Voltage–Gated Potassium Channel Genes," Handbook of Receptors and Channels, 1–71, 1995.

Epps et al., Chemistry and Physics of Lipids, 69(1994), pp. 137–150.

WO 95–18617 Abstract, (No date).

Chem. Abs., vol. 104, No. 9 Abs No. 68632 (Mar. 3, 1986).

International Search Report PCT/US97/12559, (No date).

POTASSIUM CHANNEL INHIBITORS

This application claims the benefit under 35 U.S.C. 119 (e)(1) of prior filed provisional application 60/072,719 filed Jan. 27, 1998.

BACKGROUND OF THE INVENTION

1. Field of the Invention

The present invention is broadly directed to a class of compounds useful as potassium channel inhibitors.

2. Description of Related Art

Potassium channels are expressed in eukaryotic and procaryotic cells, and are elements in the control of electrical and nonelectrical cellular functions. Subclasses of these channels have been named based on amino acid sequence and functional properties, and include for example voltage gated potassium channels (e.g., Kv1, Kv2, Kv3, Kv4). Subtypes within these subclasses have been characterized as to their putative function, pharmacology and distribution in cells and tissues (Chandy and Gutman, "Voltage-gated potassium channel genes" in Handbook of Receptors and Channels-Ligand and Voltage-gated Ion Channels, ed. R. A. North, 1995; Doupnik et al., *Curr. Opin. Neurobiol.* 5:268, 1995).

Inhibitors of potassium channels lead to a decrease in potassium ion movement across cell membranes. Consequently, such inhibitors induce prolongation of the electrical action potential or membrane potential depolarization in cells containing the inhibited or blocked potassium channels. Prolonging of the electrical action potential is a preferred mechanism for treating certain diseases, e.g., cardiac arrhythmias (Colatsky et al., *Circulation* 82:2235, 1990). Membrane potential depolarization is a preferred mechanism for the treating of certain other diseases, such as those involving the immune system (Kaczorowski and Koo, *Perspectives in Drug Discovery and Design,* 2:233, 1994).

Potassium channels which exhibit functional, pharmacological and tissue distribution characteristics have been cloned. These cloned potassium channels are useful targets in assays for identifying candidate compounds for the treatment of various disease states. For example, the delayed rectifier voltage-gated potassium channel termed $I_{kur}$ or $I_{sus}$ which has been reported to contain the Kv1.5 α-subunit gene product is generally believed to be important in the repolarization of the human atrial action potential and thus is a candidate potassium channel target for the treatment of cardiac arrhythmias especially those occurring in the atria (Wang et al., *Circ. Res.* 73:1061, 1993; Fedida et al., *Circ. Res.* 73:210, 1993; Wang et al., *J. Pharmacol. Exp. Ther.* 272:184, 1995; Amos et al., *J. Physiol.,* 491:31, 1996).

The present invention is directed to compounds which are useful as inhibitors of potassium channel function.

It is an object of the present invention, therefore, to provide compounds which are useful for the treatment of diseases in mammals, including humans, and especially for the management of diseases which can be treated by inhibiting cell membrane potassium channels.

Another object of the invention is to provide a method of treating diseases in mammals, including humans, which respond to the inhibition of potassium channel function, which method comprises administering to a mammal in need thereof a compound of the invention.

DETAILED DESCRIPTION OF THE INVENTION

This invention describes compounds and their utility as inhibitors of potassium channel function. The invention is particularly directed to compounds that inhibit potassium channels which could serve as targets for the treatment of cardiac arrhythmias (i.e., $I_{Kur}$, Kv1.5) especially those occurring in the atria (e.g., atrial flutter and atrial fibrillation) (Wang et al., *Circ. Res.* 73:1061, 1993; Fedida et al., *Circ. Res.* 73:210, 1993; Wang et al., *J. Pharmacol. Exp. Ther.* 272:184, 1995). The present invention also provides a method for treating diseases which respond to the inhibition of potassium channel function. These include, but are not limited to cardiac arrhythmias, cell proliferative disorders including cancer, disorders of the auditory system, central nervous system mediated motor dysfunction and disorders of pulmonary, vascular and visceral smooth muscle contractility.

The invention is particularly based on our discovery that the compounds of the following formula (I) are inhibitors of potassium channel function and are thus useful for inhibiting potassium transport across cellular membranes and for treating cardiac arrhythmias. In particular, these compounds have demonstrated activity against human potassium channels.

Thus, this aspect of the present invention concerns such methods and such compounds having potassium channel inhibitory activity of the formula (I) and pharmaceutically acceptable salts, esters, amides, complexes, chelates, hydrates, stereoisomers, crystalline or amorphous forms, metabolites, metabolic precursors or prodrugs thereof:

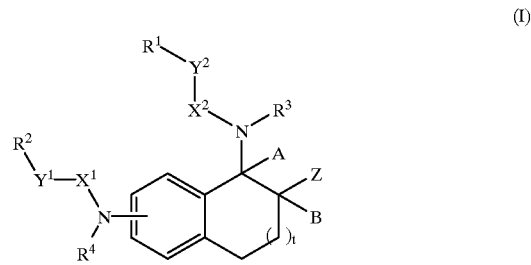

(I)

wherein t is 1, or 2;

A and B are each H, or taken together form a bond between the substituted carbons;

$R^1$ is H, alkyl or is selected from the group consisting of an optionally substituted aryl, an optionally substituted heteroaryl, an optionally substituted heterocyclyl and an optionally substituted carbocycloalkyl;

$Y^2$ is $(CH_2)_q$, $(CH_2)_wO$, HC=CH, ethynyl or NH, w is 0, 1, or 2 and q is 0, 1, or 2, with the proviso that if $Y^2$ is $(CH_2)_q$ and q=0, then $R^1$ cannot be H;

$X^2$ is C=O, C=S, or $SO_2$; with the proviso that if $Y^2$ is $(CH_2)_wO$, then $X^2$ is not $SO_2$;

$R^3$ is H, alkyl, an optionally substituted aryl, an optionally substituted aralkyl, an optionally substituted heteroaryl, an optionally substituted heteroalkyl; an optionally substituted heterocycle, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC (O)(aryl), alkylene-NHC(O)(heterocyclyl), alkylene-NHC(O)(heteroaryl), alkylene-NHC(O)-(alkylene-heterocyclyl), alkylene-NHC(O)-(heteroarayl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R_9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, $SO_2$ or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that if $Y^1$ is $(CH_2)_p$, p is 0 and $X^1$ is not $(CH_2)_n$, then $R^2$ is not H, (ii) that if $R^2$ is $R^a$—O and $Y^1$ is $(CH_2)_p$ with p=0, then $X^1$ is not $SO_2$ and (iii) if Z is not H, $OR^{14}$, $SR^{14}$ or $NR^{15}R^{16}$, then $X^2$ must be $SO_2$.

In another aspect, the present invention concerns such methods and such compounds having potassium channel inhibitory activity of the formula (II) and pharmaceutically acceptable salts, esters, amides, complexes, chelates, hydrates, stereoisomers, crystalline or amorphous forms, metabolites, metabolic precursors or prodrugs thereof:

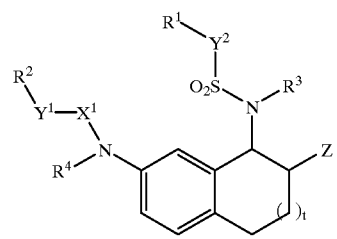

(II)

wherein t is 1, or 2;

$R^1$ is H, alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$, $(CH_2)_wO$, HC=CH, ethynyl or NH, w is 0, 1, or 2 and q is 0, 1, or 2, with the proviso that if $Y^2$ is $(CH_2)_q$ and q=0, then $R^1$ cannot be H;

$X^2$ is C=O, C=S, or $SO_2$; with the proviso that if $Y^2$ is $(CH_2)_wO$ then $X^2$ is not $SO_2$;

$R^3$ is H; alkyl, an optionally substituted aryl, or an optionally substituted heteroaryl;

Z is H, $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted heteroaryl, an optionally substituted heterocyclyl, an optionally substituted carbocycloalkyl $R^a$—O—, and $R^bR^c$—N—; where $R^a$ and $R^b$ are independently selected from the group consisting of alkyl an optionally substituted aryl, an optionally substituted heteroaryl, an optionally substituted heterocyclyl and an optionally substituted carbocycloalkyl; $R^c$ is selected from the group consisting of H, alkyl, an optionally substituted aryl, an optionally substituted heteroaryl, an optionally substituted heterocyclyl and an optionally substituted carbocycloalkyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2, or 3; and o is 0, 1, or 2

$X^1$ is C=O, C=S, $SO_2$ or $(CH_2)_n$; where n is 0, 1, or 2;

$R^4$ is H, alkyl, an optionally substituted aryl, or an optionally substituted heteroaryl; and with the provisos (i) that if $Y^1$ is $(CH_2)_p$, p is 0 and $X^1$ is not $(CH_2)_n$, then $R^2$ is not H, and (ii) that if $R^2$ is $R^a$—O— and $Y^1$ is $(CH_2)_p$ with p=0, then $X^1$ is not $SO_2$.

A preferred subgroup of compounds for practicing such methods includes compounds represented by formula (III) and pharmaceutically acceptable salts, esters, amides, complexes, chelates, hydrates, stereoisomers, crystalline or amorphous forms, metabolites, metabolic precursors or prodrugs thereof:

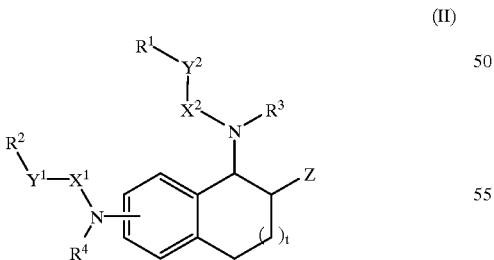

(III)

wherein t, $Y^1$, $R^2$, $R^3$ and $R^4$ are as recited above in connection with formula (I), $Y^2$ is $(CH_2)_q$, HC=CH, or ethynyl and q is 0, 1, or 2, $R^1$ is selected from the group of an optionally substituted aryl and an optionally substituted heteroaryl; $X^1$ is C=O, C=S, or $(CH_2)_n$; wherein n is 0, 1, or 2; and Z is H or $OR^{14}$, where $R^{14}$ is H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; where each $R^9$ is independently selected from H or alkyl; and L is a counter ion.

Another preferred subgroup of compounds for practicing such methods includes compounds represented by formula (IV) and pharmaceutically acceptable salts, esters, amides, complexes, chelates, hydrates, stereoisomers, crystalline or amorphous forms, metabolites, metabolic precursors or prodrugs thereof:

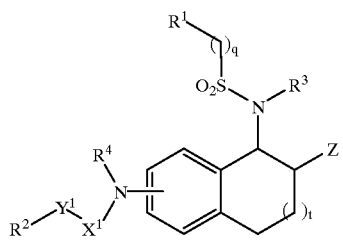

(IV)

wherein t, $R^2$, $R^3$ and $R^4$ are as recited above in connection with formula (I), q is 0, 1, or 2, $R^1$ is H or an optionally substituted aryl selected from the group of phenyl and naphthyl, with the proviso that when q=0, then $R^1$ cannot be H; $X^1$ is C=O, or $(CH_2)_n$; Z is H or OH; wherein n is 0, 1, or 2; and $Y^1$ is CH=CH ethynyl, or $(CH_2)_p$; where p is 0, 1, 2 or 3.

A particularly preferred subgroup of compounds for practicing such methods includes compounds represented by formula (V) and pharmaceutically acceptable salts, esters, amides, complexes, chelates, hydrates, stereoisomers, crystalline or amorphous forms, metabolites, metabolic precursors or prodrugs thereof:

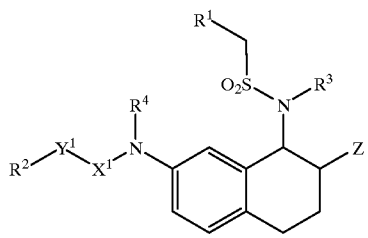

(V)

wherein $R^2$, $R^3$ and $R^4$ are as recited above in connection with formula (I) ($R^3$ preferably is H), where $R^1$ is an optionally substituted aryl selected from the group of phenyl and naphthyl; Z is H, or OH; $X^1$ is C=O, or $(CH_2)_n$; wherein n is 0, 1, or 2; and $Y^1$ is CH=CH, ethynyl or $(CH_2)_p$, where p is 0, 1, 2 or 3.

In the above formulae, $R^1$ and $R^2$ are preferably moieties that are non-ionized at a physiological pH. In preferred aspects of the present invention, $R^2$ is selected from the group consisting of H, alkyl, an optionally substituted aryl, an optionally substituted heteroaryl, an optionally substituted heterocyclyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted heteroaryl, an optionally substituted heterocyclyl and an optionally substituted carbocycloalkyl and where $R^c$ is selected from the group consisting of H, alkyl, an optionally substituted aryl, an optionally substituted heteroaryl, an optionally substituted heterocyclyl and an optionally substituted carbocycloalkyl and $R^3$ and $R^4$ are independently selected from H, alkyl, an optionally substituted aryl, or an optionally substituted heteroaryl in the above formulae (I), (II), (III), (IV) and (V). Compounds according to the present invention are particularly directed to those compounds of formulae (I), (II), (III), (IV) and (V) subject to the proviso that when $R^1$ is an optionally substituted aryl, then said optionally substituted aryl is not a dialkoxyphenyl, and especially is not a 3,4-dialkoxyphenyl.

Further preferred compounds are those having the previously identified formulae (I) (where A and B are hydrogen), (I), (III), (IV), or (V); but having the stereochemical configuration of substituents attached to the saturated ring of the core structure in accordance with the following representative formula (VI):

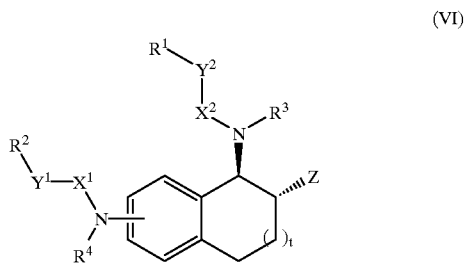

(VI)

Still other preferred compounds of the present invention are those of formulae (I), (II), (V) and (VI) having the ring substituents in the orientation of previous formulae (III) and (V).

The term "alkyl" as used alone or in combination herein refers to a straight or branched chain saturated hydrocarbon group containing from one to ten carbon atoms. Preferably, the alkyl group is a "$C_{1-6}$ alkyl" or "lower alkyl" which refer to such groups containing from one to six carbon atoms, such as methyl, ethyl, n-propyl, isopropyl, n-butyl, isobutyl, sec-butyl, tert-butyl and the like.

The related term "alkylene," as used alone or in combination herein, refers to a straight or branched chain saturated divalent hydrocarbon group containing from one to ten carbon atoms. Preferably, the alkylene group is a "$C_{1-6}$ alkylene" or "lower alkylene" which refer to such groups containing from one to six carbon atoms, such as methylene, ethylene, n-propylene, isopropylene, n-butylene, isobutylene, sec-butylene, tert-butylene and the like.

The term "alkoxy" as used alone or in combination herein refers to a straight or branched chain alkyl group covalently bonded to the parent molecule through an —O— linkage containing from one to ten carbon atoms and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "alkoxyalkyl" refers to an alkyl group substituted with an alkoxy group.

The term "haloalkyl" is a substituted alkyl, preferably a substituted lower alkyl, substituted with one or more halogen atoms, and preferably is a $C_1$ to $C_4$ alkyl substituted with one to three halogen atoms. One example of a haloalkyl is trifluoromethyl.

The term "alkanoyl" as used alone or in combination herein refers to an acyl radical derived from an alkanecarboxylic acid, particularly a lower alkanecarboxylic acid, and includes such examples as acetyl, propionyl, butyryl, valeryl, and 4-methylvaleryl.

The term "aminocarbonyl" means an amino-substituted carbonyl (carbamoyl or carboxamide) wherein the amino group can be a primary, secondary (mono-substituted amino) or tertiary amino (di-substituted amino) group preferably having as a substituent(s) a lower alkyl.

The term "carbocycloalkyl" refers to stable, saturated or partially unsaturated monocyclic, bridged monocyclic, bicyclic, and spiro ring hydrocarbyls of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. The term "optionally substituted" as it refers to "carbocycloalkyl" herein indicates that the carbocycloalkyl group may be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heterocyclyl" as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocyclyl is a 5 or 6-membered monocyclic ring or an 8–11 membered bicyclic ring which consists of carbon atoms and contains one, two, or three heteroatoms selected from nitrogen, oxygen and/or sulfur. The term "optionally substituted" as it refers to "heterocyclyl" herein indicates that the heterocyclyl group may be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclyl groups are isooxazolyl, imidazolinyl, thiazolinyl, imidazolidinyl, pyrrolyl, pyrrolinyl, pyranyl, pyrazinyl, piperidyl, morpholinyl and triazolyl. The heterocyclyl group may be attached to the parent structure through a carbon atom or through any heteroatom of the heterocyclyl that results in a stable structure.

The term "heteroaryl" as used herein refers to a stable, aromatic monocyclic or bicyclic ring system containing carbon atoms and other atoms selected from nitrogen, sulfur and/or oxygen. Preferably, a heteroaryl is a 5 or 6-membered monocyclic ring (optionally benzofused) or an 8–11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower]alkylamino, cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heteroaryl groups are isoxazolyl, imidazolyl, thiazolyl, isothiazolyl, pyridyl, furyl, pyrimidinyl, pyrazolyl, pyridazinyl, furazanyl and thienyl. The heteroaryl group may be attached to the parent structure through a carbon atom or through any heteroatom of the heteroaryl that results in a stable structure.

The term "heteroaralkyl" as used herein refers to a lower alkyl as defined above in which one hydrogen atom is replaced by a heteroaryl radical as defined above. The term "optionally substituted" as it refers to "heteroaralkyl" herein indicates that the heteroaryl group may be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower]alkylamino, cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heteroaralkyl groups are 2-pyridylmethyl, 3-pyridylmethyl, 4-pyridylmethyl, 3-pyridylethyl and 4-pyrimidinylmethyl.

The specific chemical nature of the optionally substituted heterocyclyl and heteroaryl groups for the terminal moieties $R^1$ and $R^2$ in the prior identified potassium channel inhibitor compounds is not narrowly critical and, as noted above, a wide variety of substituent groups are contemplated. Preferably, the substituents for the heterocyclyl and heteroaryl groups are selected such that the total number of carbon and hetero atoms comprising the substituted heterocyclyls and heteroaryls is no more than about 25.

The terms "halo" and "halogen" as used herein to identify substituent moieties, represent fluorine, chlorine, bromine or iodine, preferably chlorine or fluorine.

The term "aryl" when used alone or in combination refers to an unsubstituted or optionally substituted monocyclic or bicyclic aromatic hydrocarbon ring system. Preferred are optionally substituted phenyl or naphthyl groups. The aryl group may optionally be substituted at one or more substitutable ring positions by one or more groups independently selected from alkyl (preferably lower alkyl), aralkyl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Preferably, the aryl group is phenyl optionally substituted with up to four and usually with one or two groups, preferably selected from $C_{1-6}$ alkyl, $C_{1-6}$ alkoxy, as well as cyano, trifluoromethyl and halo.

The term "aralkyl" alone or in combination refers to a lower alkyl radical as defined above in which one hydrogen atom is replaced by an aryl radical as defined above, and includes benzyl, and 2-phenylethyl. The aralkyl group may optionally be substituted at one or more substitutable ring positions by one or more groups independently selected from alkyl (preferably lower alkyl), aralkyl, alkoxy (preferably lower alkoxy), nitro, monoalkylamino preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "alkoxycarbonyl" alone or in combination means a radical of the formula —C(O)-alkoxy, in which alkoxy is as defined above.

The term "alkylcarbonyloxy" alone or in combination means a radical of the formula —O—C(O)-alkyl, in which alkyl is as defined above.

The term "alkenyl" means a two to seven carbon, straight or branched hydrocarbon containing one or more double bonds, preferably one or two double bonds. Examples of alkenyl include ethenylene, propenylene, 1,3- butadienyl, and 1,3,5-hexatrienyl.

The term "substituted amino" refers to a group of the formula NZ'Z" wherein Z' is H, alkyl, carbocycloalkyl, aryl, heteroaryl, heterocyclyl, heteroaralkyl, or heterocyclyl (alkylene) and Z" is H, alkyl, carbocycloalkyl, or aryl further substituted with a carboxylic acid or carboxylic ester, provided that when Z' is H, then Z" is other than H, or Z' and Z" taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, each optionally substituted with alkyl, alkoxy, alkylthio, halo, aryl or hydroxy.

The term "treating" as used herein, describes the management and care of a patient afflicted with a condition, disease or disorder for which the administration of a compound of the present invention alters the action or activity of a potassium channel to prevent the onset of symptoms or complications associated with the condition, disease or disorder, to alleviate the symptoms or complications caused by the condition, disease or disorder, or to eliminate the condition, disease or disorder altogether.

It is recognized that there may be one or two chiral centers in the compounds falling within the scope of the present invention and thus such compounds will exist as various stereoisomeric forms. Applicants intend to include all the various stereoisomers within the scope of the invention, referred to herein as the "pharmaceutically acceptable stereoisomers." Thus, this invention is intended to include the cis and trans isomers and the corresponding enantiomers of the compounds of formula I–IV. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention.

The present invention also encompasses the pharmaceutically acceptable esters, amides, complexes, chelates, hydrates, crystalline or amorphous forms, metabolites, metabolic precursors or prodrugs of the compounds of formulae (I), (II), (III) and (IV). Pharmaceutically esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmacokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, *Design of Prodrugs,* (1985). Those skilled in the art are well-versed in the preparation of prodrugs and are well-aware of its meaning.

The compounds of the present invention can be used in their neat form or in the form of pharmaceutically-acceptable salts derived from inorganic or organic acids. Examples of acids which may be employed to form pharmaceutically acceptable acid addition salts of compounds of the present invention include such inorganic acids as hydrochloric acid, sulphuric acid and phosphoric acid and such organic acids as oxalic acid, maleic acid, succinic acid and citric acid. These salts thus include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Also, the basic nitrogen-containing groups can be quaternized with such agents as lower alkyl halides, such as methyl, ethyl, propyl, and butyl chlorides, bromides and iodides; dialkyl sulfates, like dimethyl, diethyl, dibutyl and diamyl sulfates, long chain halides such as decyl, lauryl, myristyl and stearyl chlorides, omides and iodides, aralkyl halides like benzyl and phenethyl bromides and others. Water or oil soluble or dispersible products are thereby generally obtained.

The pharmaceutically acceptable salts of the compounds of the present invention also can exist as various solvates, such as with water, methanol, ethanol, dimethylformamide, ethyl acetate and the like. Mixtures of such solvates also can be prepared. Such solvates are within the scope of the present invention.

The pharmacological profile of the potassium channel inhibitory activity of the compounds of the present invention can be readily assessed by those skilled in the art using routine experimentation, such as the procedures and techniques illustrated in the examples which follow. Assays for assessing the activity of particular compounds may employ cells stably transfected to express a specific potassium channel, as well as native mammal cells. In particular, cells stably transfected to express a specific potassium channel, which have been treated with a voltage dependent fluorescent dye, such as bis-(1,3-dibutylbarbituric acid)trimethine oxonol can be used to gauge the inhibitory activity of potassium channel inhibitor compounds, possibly in comparison to known inhibitors. Alternatively, such cells can be primed with a detectible species, such as $^{86}$Rb, and then challenged with a particular compound, under conditions otherwise suitable for activating the potassium channel, to assess the potassium inhibitory activity of the compound. The potassium channel inhibitory activity of a compound also can be determined using isolated mammalian cells and the whole cell configuration of the known patch clamp technique (Hamill et al., *Pflugers Archiv* 391:85, 1981). These and other known techniques can be readily employed by those skilled in the art to assess the activity level of the potassium channel inhibitor compounds of the present invention.

The compounds of the present invention may be administered by a variety of routes including orally, parenterally, sublingually, intranasally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intracardiac injection, or infusion techniques. Topical administration may also involve the use of transdermal administration such as transdermal patches or iontophoresis devices.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,2-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The compounds of the present invention can also be administered in the form of liposomes. As is known in the art, liposomes are generally derived from phospholipids or other lipid substances. Liposomes are formed as mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York N.Y. (1976), p. 33, et seq.

To select preferred compounds from less preferred compounds, one uses by example the in vitro assays detailed under the sub-heading BioAssays hereafter. Typically, a preferred compound will produce half maximal blocking activity at a concentration ranging from about 10 nM to about 1 $\mu$M in the in vitro assays described. One of ordinary skill will recognize that the final and optimum dose and regimen will be determined empirically for any given drug.

Total daily dose administered to a host in single or divided doses may be an amount, for example, from 0.001 to 100 mg of active ingredient per kg body weight on a daily basis and more usually 0.01 to 10 mg/kg/day. Dosage unit compositions may contain such amounts of submultiples thereof to make up the daily dose. It is anticipated that a therapeutically effective serum concentration of active ingredient will be 10 nM to 10 $\mu$M (5 ng/ml to 5 $\mu$g/ml).

The amount of active ingredient that may be combined with carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, and diet of the patient, the time of administration, the route of administration, the rate of excretion, whether a drug combination is used, and the severity of the particular disease.

The present invention is explained in greater detail in the Examples which follow. These examples are intended as illustrative of the invention, and are not to be taken as limiting thereof Unless otherwise indicated, all references to parts and percentages are based on weight and all temperatures are expressed in degrees Celsius. The scope of the invention is not construed as merely consisting of the following examples.

EXAMPLES

Unless otherwise specified, all solvents and reagents were purchased from commercial suppliers and used without further purification. Analytical thin layer chromatography (TLC) was performed on Whatman Inc. 60 silica gel plates (0.25 mm thickness). Compounds were visualized under UV lamp or by developing with $KMnO_4$/KOH ninhydrin, or Hanessian's solution. Flash chromatography was done using silica gel from Selectro Scientific (particle size 32–63). $^1$H NMR and $^{13}$C NMR spectra were recorded at 300 MHz and 75.5 MHz, respectively.

Compound Preparation

Tetrahydronaphthalene (tetralin) and benzocycloheptane, compounds of the previous formulae (I), (II), (Ill) and (IV) useful as potassium channel inhibitors in accordance with the present invention can be prepared in accordance with several sequential steps as illustrated with reference to the tetralin species in the preparation which follow.

Preparation 1
Synthesis of 7-nitro-1,2,3,4-tetrahydro-2-naphthalenol

This preparation demonstrates the reduction of a nitrotetralone to give the corresponding alcohol.

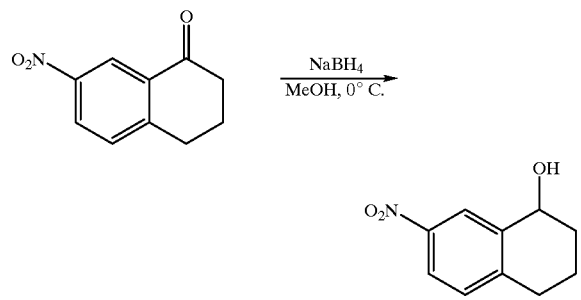

A suspension of 7-nitro-1-tetralone (10.14 g, 0.053 mol) in MeOH (600 ml) was cooled to 0° C. and treated with NaBH$_4$ (4.25 g, 0.11 mol. 2.1 equiv.). A nitrotetralone can be obtained by nitration of a 1-tetralone, the desired product being separated from minor component byproducts. The reaction mixture became homogeneous almost immediately. After stirring at 0° C. for 30 min. 2N HCl (100 ml) was added and stirring was continued for an additional 30 min. The reaction mixture was concentrated under reduced pressure (approx. 150 ml) and diluted with CH$_2$Cl$_2$ (200 ml) and H$_2$O (100 ml). The aqueous layer was separated and extracted with additional CH$_2$Cl$_2$ (2×100 ml). The combined organic layers were washed with brine (100 ml), dried (Na$_2$SO$_4$), filtered and concentrated under reduced pressure to 7-nitro-1,2,3,4-tetrahydo-2-naphthalenol as a white solid (10.13 g, 99%) which was used in the next step without further purification. R$_f$ (silica gel): 0.50 (40% hexane: 40% CH$_2$Cl$_2$: 20% EtOAc); $^1$H NMR (300 MHZ, CDCl$_3$) 8.29 (d,J=2.1 Hz, 1H), 7.97(dd,J=2.1 and 8.1 Hz, 1H), 7.21 (d, J=8.1 Hz, 1H), 4.80–4.77 (m, 1H), 2.94–2.73 (m, 2H), 2.47 (d, J=6.0 Hz, 1H), 2.12–1.93 (m, 2H), 1.90–1.74 (m, 2H); $^{13}$C NMR (75 MHZ, CDCl$_3$) 146.5, 145.1, 140.6, 129.9, 123.6, 122.2, 67.8, 31.9, 29.3, 18.6.

Preparation 2
Synthesis of 7-nitro-3,4-dihydronaphthalene

This preparation describes subjecting the alcohol product of Preparation 1 to an acid catalyzed dehydration to give the corresponding tetralene.

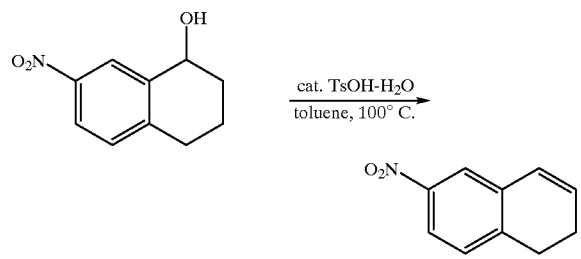

7-nitro-1,2,3,4-tetrahydo-2-naphthalenol (10.13 g, 0.053 mol) (from Preparation 1) was heated in the presence of TsOH—H$_2$O (1.72 g, 0.009 mol, 0.2 equiv.) in toluene (150 ml) for 2 h at 100° C. The solvent was removed under reduced pressure and the residue was treated with EtOAc (150 ml) and saturated aqueous NaHCO$_3$ (150 ml). The aqueous layer was separated and extracted with additional EtOAc (2×100 ml). The combined organic layers were washed with saturated aqueous NaCl (200 ml), dried (Na$_2$SO$_4$), filtered, and concentrated under reduced pressure to give 7-nitro-3,4-dihydronaphthalene as a brown oil (9.18 g, 100%) which was used in the next step without additional purification. R$_f$(silica gel): 0.79 (70% hexane: 30% EtOAc); $^1$H NMR (300 MHZ, CDCl$_3$) 7.95 (dd, J=2.4 and 8.1 Hz, 1H), 7.83 (d, J=2.4 Hz, 1H), 7.21 (d, J=8.1 Hz, 1H), 6.50 (d, J=6.50 Hz, 1H), 6.18 (dt, J=4.5 and 9.6 Hz, 2H), 2.88 (t, J=8.4 Hz, 2H), 2.40–2.34 (m, 2H); $^{13}$C NMR (75 MHZ, CDCl$_3$) 147.1, 143.1, 135.3, 131.4, 128.2, 126.5, 121.8, 120.3, 27.4, 22.5.

Preparation 3
Synthesis of 1,2-epoxy-7-nitro-3,4-dihyroronaphthalene

In this preparation, the double bond in the tetralene of Preparation 2 is oxidized to give the corresponding epoxide.

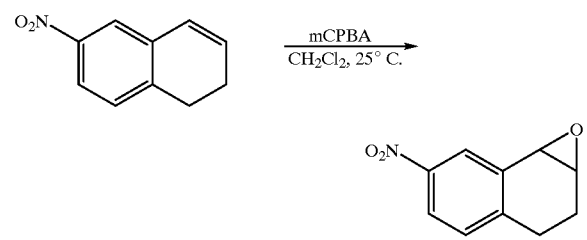

A solution of 7-nitro-3,4-dihydronaphthalene (9.18 g; 0.052 mol) (from Preparation 2) in CH$_2$Cl$_2$ (600 ml) was cooled to 0° C. and treated with m-CPBA, 57–85%, (13.86 g, approx. 0.056 mol, approx. 1.1 equiv). The reaction mixture was allowed to stir for 48 h, slowly warming to room temperature. The mixture was treated with aqueous NaHCO$_3$ (300 ml) and the organic layer was separated. The organic layer was extracted with additional aqueous NaHCO$_3$, washed with aqueous NaCl, dried (Na$_2$SO$_4$), filtered and concentrated under reduced pressure to give 1,2-epoxy-7-nitro-3, 4-dihydronaphthalene (9.94, 100%) as a white solid which was used in the next step without further purification. R$_f$ (silica gel): 0.56(70% hexane: 30% EtOAc); $^1$H NMR (300 MHZ, CDCl$_3$) 8.24 (s, 1H), 8.08 (dd, J=1.8 and 8.1 H 1H), 7.23 (d, J=8.1 Hz, 1H), 3.92 (d, J=4.2 Hz, 1H), 3.77 (s, 1H), 2.87–2.62 (m, 2H), 2.47 (dd, J=6.6 and 14.4 Hz, 1H), 1.78 (dt, J=5.7 and 14.1 Hz, 1H), $^{13}$C NMR (75 MHZ, CDCl$_3$) 146.5, 144.7, 134.5, 129.4, 124.4, 123.4, 54.7, 51.8, 24.5, 21.0.

Preparation 4
Synthesis of trans-1-amino-7-nitro-1,2,3,4-tetrahydro-2-naphthalenol In this preparation, the epoxide is reacted with ammonium hydroxide to give the corresponding amino alcohol.

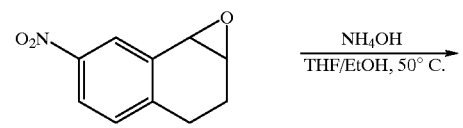

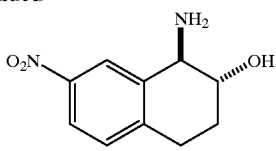

A solution of 1,2-epoxy-7-nitro-3,4-dihydroronaphthalene (10.84 g; 0.057 mol) (from Preparation 3) in THF (50 ml) and EtOH (50 ml) was heated to 40° C. and NH$_4$OH (60 ml) was added dropwise over the course of 1 h. After the addition was complete, the temperature was increased to 60° C. and the reaction was stirred for 24 h. An additional 50 ml of NH$_4$OH was added and the reaction was stirred for another 24 h. The solvent was removed under reduced pressure to give a brown powder (10.73 g) that was dried under high vacuum at 50° C. for 48 h. The trans-1-amino-7-nitro-1,2,3,4-tetrahydro-2-naphthalenol was used in the next two preparations without further purification.

Preparation 5

The General Synthesis of Secondary Amines as Illustrated for the Synthesis of Give trans-N-(benzyl)-1-amino-7-nitro-1,2,3,4-tetrahydro-2-naphthalenol In this preparation, the amino alcohol is reacted with an aldehyde to attach an R'-moiety to the amino group, where R' is equivalent to $R^3$ as defined in formula (I).

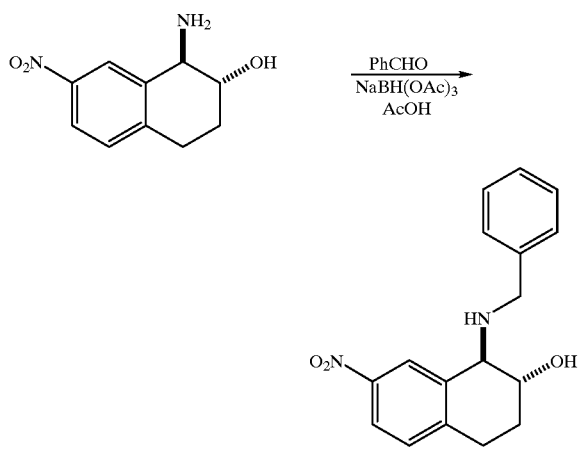

The amino alcohol is reacted in a suitable solvent with the aldehyde under reductive amination conditions. Suitable solvents in which the reaction can be conducted include glacial acetic acid, MeOH, or 1,2-dichloroethane. Suitable reducing agents include sodium triacetoxyborohydride, sodium cyanoborohydride, or sodium borohydride.

A solution of trans-1-amino-7-nitro-1,2,3,4-tetrahydro-2-naphthalenol (0.58 g; 2.8 mmol) (from Preparation 4) in glacial acetic acid was treated with benzaldehyde (0.31 ml; 3.0 mmol; 1.1 equiv.) followed by sodium triacetoxyborohydride (0.82 g; 3.9 mmol; 1.4 equiv.). The reaction mixture was allowed to stir at room temperature for 16 h. The reaction mixture was diluted with EtOAc (50 ml) and the pH was adjusted to pH=9 by the addition of 1 N NaOH. The organic layer was separated, washed with aqueous NaCl (50 ml), filtered, dried (Na$_2$SO$_4$) and concentrated under reduced pressure. The crude product was purified by flash chromatography on silica gel to give trans-N-(benzyl)-1-amino-7-nitro-1,2,3,4-tetrahydro-2-naphthalenol (0.37 g; 44%). R$_f$ (silica gel) 0.58 (60% EtOAc: 20% hexane: 20% CH$_2$Cl$_2$); $^1$H NMR (300 MHz, d$_6$-acetone) 8.38 (d, J=2.1 Hz, 1H), 7.96 (dd, J=2.1 and 8.7 A, 1H), 7.43 (d, J=7.2 Hz, 2H), 7.35–7.30 (m, 3H), 7.25–7.20 (m, 1H), 4.20–4.14 (m, 1H), 3.93 (d, J=13.5 Hz, 1H), 3.81 (s, 1H), 3.80 (d, J=6 Hz, 1H), 3.77 (d, J=13.5 Hz, 1H), 3.07–2.84 (m, 2H), 2.27–2.17 (m, 1H), 1.97–1.96 (m, 1H); $^{13}$C NMR (75 MHz d$_6$-acetone) 146.5, 145.6, 141.3, 139.8, 129.6, 128.3 (two carbons), 128.2 (two carbons), 126.8, 124.2, 121.1, 67.2, 61.9, 49.8, 27.5, 26.3.

Preparation 6

The General Procedure for the Synthesis of Sulfonamides as Illustrated for the Synthesis of trans-N-(4ethylphenylsulfonyl)-1-amino-7-nitro-1,2,3,4-tetrahydro-2-naphthalenol While the amino alcohol of Preparation 4 or 5 can be optionally protected with conventional protecting group(s) as are commonly employed to block or protect the amino (—NH$_2$) and/or the hydroxy (—OH) functionality while reacting other functional groups on the parent compound, this (and the subsequent) preparations shows that it is possible to react the amino alcohol directly without use of any protecting group(s).

In this preparation, the amino alcohol is reacted with a sulfonyl chloride to attach an R'—SO$_2$— moiety to the amino group, where R' is equivalent to $R^1$—$Y^2$ as defined in formula (I) and elsewhere. The amino alcohol is reacted in a suitable solvent with the sulfonyl chloride (R'SO$_2$Cl) or sulfonyl anhydride in the presence of an acid scavenger. Suitable solvents in which the reaction can be conducted include methylene chloride, DMF and tetrahydrofuran. Suitable acid scavengers include triethylamine, and pyridine.

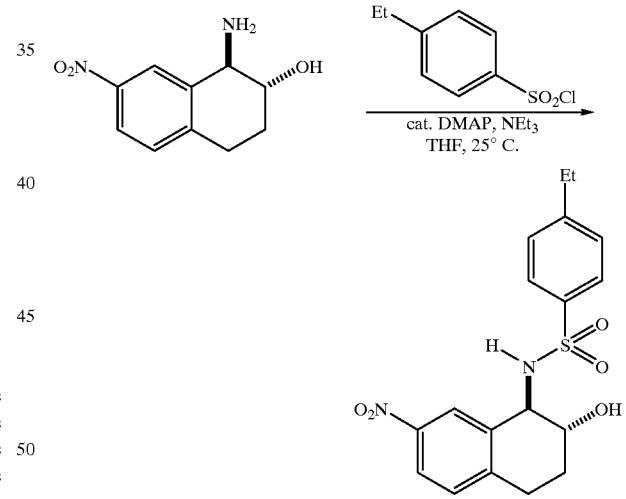

A solution of trans-1-amino-7-nitro-1,2,3,4-tetrahydro-2-naphthalenol (0.91 g; 4.37 mmol) (from Preparation 4) in THF (20 ml) was cooled to 0° C. and treated with DMAP (0.010 g; 0.082 mmol, 0.02 equiv), NEt$_3$ (0.90 ml; 6.46 mmol; 1.5 equiv) and 4-ethylbenzene sulfonyl chloride (1.05 g; 5.13 mmol; 1.2 equiv). After 15 min at 0° C., the reaction was allowed to warm up to room temperature and stirred for an additional 24 h. The solvent was removed under reduced pressure and the residue was treated with EtOAc (150 ml) and a 20% aqueous solution of conc. HCl (50 ml). The organic layer was separated, washed with aqueous NaCl (50 ml), filtered, dried (Na$_2$SO$_4$), and concentrated. The crude product was purified by flash chromatography on silica gel to give trans-N-(4-ethylphenylsulfonyl)-1-amino-7-nitro-1, 2,3,4-tetrahydro-2-naphthalenol as a tan solid (1.10 g; 67%). $R_f$ (silica gel): 0.67 (60% EtOAc: 20% hexane: 20% $CH_2Cl_2$); $^1H$ NMR (300 MHZ, $CDCl_3$) 7.93 (d, J=2.1 Hz, 1H), 7.89 (d, J=8.4 Hz, 2H), 7.44 (d, J=8.4 Hz, 2l), 7.40 (d, J=2.1 Hz, 1H), 7.20 (d, J=8.7 Hz, 1H), 5.21 (d, J=8.1 Hz, 1H), 4.28 (t, J=7.8 Hz, 1H), 4.07–4.04 (m, 1H), 3.03 (d, J=2.7 Hz, 1H), 2.98–2.88 (m, 2H), 2.77 (q, J=7.5 Hz, 2H), 2.51–2.16 (m, 1H), 1.29 (t, J=7.5 Hz, 3H); $^{13}C$ NMR(75 MHZ, $CDCl_3$) 150.7, 146.5, 144.7, 136.9, 135.7, 129.7, 129.1 (two carbons), 127.1 (two carbons), 123.8, 122.3, 70.4, 58.4, 28.6, 27.1, 26.3, 14.7.

Preparation 7
The General Procedure for the Reduction of the Aromatic Nitro Functionality as Illustrated for the Synthesis of trans-N1-(4-ethylphenylsulfonyl-1,7-diamino-1,2,3,4-4tetrahydro-2-naphthalenol The sulfonylated product of Preparation 6 is reduced in this preparation to give the corresponding aniline.

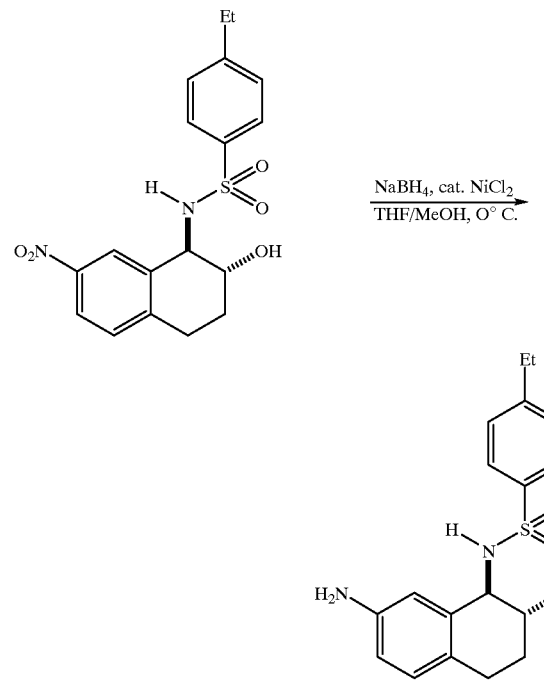

A solution of trans-N-(4-ethylphenylsulfonyl)-1-amino-7-nitro-1,2,3,4-tetrahydro-2-naphthalenol (0.96 g; 2.6 mmol) (from Preparation 6) in THF (15 ml) and MeOH (10 ml) was cooled to 0° C. and treated with $NaBH_4$ (0.46 g; 12.2 mmol; 4.7 equiv.) followed immediately by $NiCl_2$ (0.15 g; 1.2 mmol, 0.5 equiv.). After 15 min at 0° C., the reaction was allowed to warm up to room temperature and stirred for an additional 1 h. The solvent was removed under reduced pressure to leave a black residue which was treated with EtOAc (100 ml) and aqueous NaCl (100 ml). The aqueous layer was separated and extracted with additional EtOAc (3×50 ml). The combined organic layers were dried ($Na_2SO_4$), filtered, and concentrated under reduced pressure to give trans-N1-(4-ethylphenylsulfonyl)1,7-diamino-1,2,3,4-tetrahydro-2-naphthalenol as a tan solid (0.79 g; 89%) which was used without further purification in the next step. $R_f$ (silica gel): 0.43 (60% EtOAc: 20% hexane: 20% $CH_2Cl_2$); $^1H$ NMR (300 MHZ, $d_4$-MeOH) 7.86 (d, J=8.4 Hz, 2H), 7.45 (d, J=8.4 Hz, 2H), 6.80 (d, J=8.1 Hz, 1H), 6.55 (dd, J=24 and 8.4 Hz, 1H), 6.03 (d, J=1.8 Hz, 1H), 4.10 (d, J=4.8 Hz, 1H), 3.92–3.88 (m, 1H), 2.81–2.71 (m, 3H), 2.60–2.51 (m, 1H), 2.06–1.96 (m, 1H), 1.81–1.73 (m, 1H), 1.30 (t, J=7.5 Hz, 3H); $^{13}C$ NMR (75 MHZ, $d_6$DMSO) 148.8, 146.8, 140.8, 135.5, 129.1, 128.8, 127.1, 124.5, 115.5, 114.5, 68.4, 57.1, 28.4, 25.9, 23.4, 15.5.

Preparation 8
Synthesis of trams-N1-(4-ethylphenylsulfonyl)-N7-(4-trifluoromethoxybenzyl)-1,7-diamino-1,2,3,4-tetrahydro-2-naphthalenol In this preparation, the amino group on the aniline product of Preparation 7 is substituted.

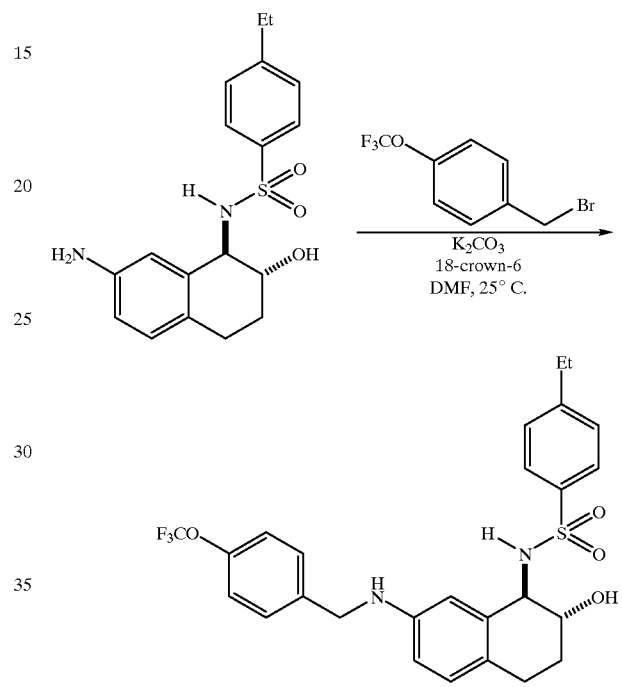

A solution of trans-N1-(4-ethylphenylsulfonyl)-1,7-diamino-1,2,3,4-tetrahydro-2-naphthalenol (0.049 g; 0.14 mmol) (from Preparation 6) in anhydrous DMF (2 ml) was treated with $K_2CO_3$ (0.040 g; 0.29 mmol; 2.1 equiv.) and 18-crown-6 (0.060 g; 0.23 mmol; 1.6 equiv.) followed by 4-trifluoromethoxybenzyl bromide (30 μM; 0.19mmol; 1.3 equiv.). The reaction mixture was heated to 60° C. and allowed stir 24 h. The reaction mixture was diluted with EtOAc (10 ml) and 1N HCl (20 ml). The organic layer was separated, washed with additional 1N HCl (20 ml) and brine (20 ml), dried ($Na_2SO_4$), filtered and concentrated. The crude product was purified by flash chromatography on silica gel to give trans-N1-(4-ethylphenylsulfonyl)-N7-(4-trifluoromethoxybenzyl)-1,7-diamino-1,2,3,4-tetrahydro-2-naphthalenol (0.035 g; 48%) as a white solid. $R_f$(silica gel): 0.54 (30% EtOAc: 40% hexane: 30% $CH_2Cl_2$); $^1H$ NMR (300 MHZ, $d_6$-DMSO) 7.84 (d, J=7.8 Hz, 1H), 7.77 (d, J=8.1 Hz; 2H), 7.39 (d, J=6.0 Hz, 2H), 7.36 (d, J=6.0 Hz, 2H), 7.28 (d, J=8.4 Hz, 2H), 6.70 (d, J=8.4 Hz, 1H), 6.39 (dd, J2.1 and 8.4 Hz, 1H), 6.03 (d, J=1.8 Hz, 1H), 5.89 (t, J=6.0 Hz, 1H), 4.68 (d, J=3.3 Hz, 1H), 4.03–3.88 (m, 3H), 3.68 (d, J=3.3 Hz, 1H), 2.58 (q, J=7.5 Hz, 2H), 2.64–2.57 (m, 1H), 2.39–2.30 (m, 1H), 1.91–1.81 (m, 1H), 1.60–1.54 (m, 1H), 1.12 (t, J=7.5 Hz, 3H); $^{13}C$ NMR (75 MHZ, $d_6$DMSO) 148.8, 147.7, 146.9, 140.5, 140.4, 135.3, 129.7, 129.3, 128.8, 127.2, 124.9, 121.4, 113.5, 113.0, 68.8, 57.0, 46.2, 28.3, 25.6, 23.2, 15.3.

Preparation 9
Synthesis of trans-N1-(4-n-propylphenylsulfonyl)-N7-(styrylcarbamoyl)-1,7-diamino-1,2,3,4-tetrahydro-2-naphthalenol In this preparation, an aniline analogous to that of Preparation 7 is acylated, for example using RCOCl where R is equivalent to $R^{2-Y1}$ and $X^1$ is C=O as defined in formula (I) and elsewhere to attach a substituent group to the amino group.

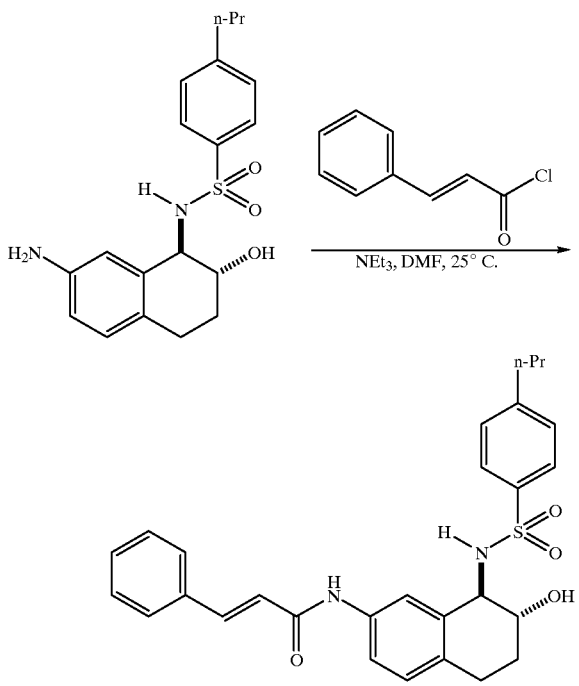

A solution of trans-N1-(4-n-propylphenylsulfonyl)-1,7-diamino-1,2,3,4-tetrahydro-2-naphthalenol (0.076 g; 0.21 mmol) in anhydrous DMF (2 ml) was cooled to 0° C. and treated with NEt$_3$ (30 μL, 0.22 mmol; 1 equiv) followed by cinnamoyl chloride (0.049 g; 0.29 mmol; 1.4 equiv). After 15 min at 0° C., the reaction was allowed to warm up to room temperature and stirred for an additional 12 h. The reaction mixture was diluted with EtOAc (15 ml) and 1N HCl (20 ml). The organic layer was separated, washed with additional 1N HCl (20 ml) and brine (20 ml), dried (Na$_2$SO$_4$), filtered and concentrated. The crude product was purified by flash chromatography on silica gel to give trans-N1-(4-n-propylphenylsulfonyl)-N7-(styrylcarbamoyl)-1,7-diamino-1,2,3,4-tetrahydro-2-naphthalenol (0.061 g; 59%) as a white solid. R$_f$(silica gel): 0.61 (60% EtOAc: 20% hexane: 20% CH$_2$Cl$_2$); ); $^1$H NMR (300 MHZ, d$_6$-DMSO) 10.06 (s, 1H), 7.96 (d, J=8.1 Hz, 1H), 7.76 (d, J=8.4Hz, 2H), 7.62–7.53 (m, 4H), 7.46–7.39 (m, 5H), 7.04 (d, J=8.4 Hz, 1H), 6.82 (d, J=15.6 Hz, 1H), 4.81 (d, J=3.0 Hz, 1H), 4.16 (d, J=4.1 Hz, 1H), 3.61 (d, J=2.7 Hz, 1H), 2.76–2.66 (m, 1H), 2.61 (t, J=7.5 Hz, 2H), 2.58–2.50 (m, 1H), 2.00–1.85 (m, 1H), 1.60–1.53 (m, 3H), 0.85 (t, J=7.5 Hz, 3H); $^{13}$C NMR (75 MHZ, d$_6$-DMSO) 163.8, 147.2, 140.6, 140.4, 137.5, 135.6, 135.4, 132.5, 130.2, 129.6 (two carbons), 129.4 (two carbons), 129.1, 128.2 (two carbons), 126.9 (two carbons), 123.0, 121.9, 119.4, 67.9, 56.8, 37.4, 25.2, 24.0, 23.5, 13.9.

When using a protecting group in connection with a specific synthesis, the species of protecting group used is not critical so long as the derivatized —NH$_2$ or —OH group is stable to the condition(s) of subsequent reaction(s) and can be removed at the appropriate point without disrupting the remainder of the molecule. For amino protecting groups see T. W. Greene and P. Wuts, *Protective Groups in Organic Synthesis,* Chapter 7 (1991). Preferred amino protecting groups are t-butoxycarbonyl (Boc), phthalimide, a cyclic alkyl, and benzyloxycarbonyl. For hydroxy protecting groups see T. W. Greene and P. Wuts, *Protective Groups in Organic Synthesis,* Chapter 2 (1991). A suitable "hydroxy protecting group" includes one of the ether or ester derivatives of the hydroxy group commonly employed to block or protect the hydroxy group while reactions are carried out on other functional groups on a compound. Hydroxy protecting groups include tert-butyldiphenylsilyloxy (TBDPS), tert-butyldimethylsilyloxy (TBDMS), triphenylmethyl (trityl), mono- or di- methoxytrityl, or an alkyl or aryl ester.

Using the principles and techniques of Preparations 1 through 9 (and methods available from the literature, such as WO 98/04521 and WO 98/36749), and appropriate starting materials, which will be well-understood by those skilled in the art, a variety of other compounds falling within the scope of the present invention can be synthesized. In this regard, compounds listed in the following Tables 1A, 1B and 1C can be synthesized.

TABLE 1A

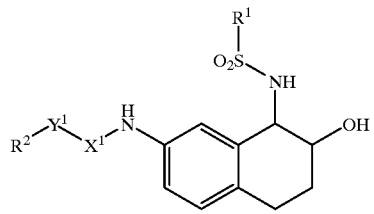

| Entry | R$^1$ | R$^2$ | —Y$^1$—X$^1$— |
|---|---|---|---|
| 1 | 4-ethylphenyl | 3-methoxyphenyl | —C(O)— |
| 2 | 3-ethylphenyl | 3-methoxyphenyl | —C(O)— |
| 3 | 3-n-propylphenyl | 3-methoxyphenyl | —C(O)— |
| 4 | 4-ethylphenyl | 4-methoxyphenyl | —C(O)— |
| 5 | 4-ethylphenyl | 4-chlorophenyl | —C(O)— |
| 6 | 4-ethylphenyl | 4-pentoxyphenyl | —C(O)— |
| 7 | 4-isopropylphenyl | 3-methoxyphenyl | —C(O)— |

TABLE 1A-continued

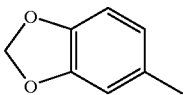

| Entry | R¹ | R² | —Y¹—X¹— |
|---|---|---|---|
| 8 | 4-n-propylphenyl | 3-methoxyphenyl | —C(O)— |
| 9 | 4-ethylphenyl | 3-ethoxyphenyl | —C(O)— |
| 10 | 4-chlorophenyl | 3-ethoxyphenyl | —C(O)— |
| 11 | 4-chlorophenyl | phenyl | —C(O)— |
| 12 | 4-bromophenyl | 3-ethoxyphenyl | —CO— |
| 13 | 4-ethylphenyl | 2-methoxyphenyl | —C(O)— |
| 14 | 4-styrenyl | 3-tolyl | —C(O)— |
| 15 | 4-isopropylphenyl | 4-tolyl | -trans-CHCHC(O)— |
| 16 | 4-isopropylphenyl | 4-chlorophenyl | -trans-CHCHC(O)— |
| 17 | 4-n-propylphenyl | phenyl | -trans-CHCHC(O)— |
| 18 | 2-dimethylamino-6-naphthyl | 4-ethylphenyl | —C(O)— |
| 19 | 4-n-butylphenyl | 3-methoxyphenyl | —C(O)— |
| 20 | 4-t-butylphenyl | 4-tolyl | —C(O)— |
| 21 | 4-n-pentylphenyl | 3-methoxyphenyl | —C(O)— |
| 22 | 4-ethylphenyl | phenyl | -cyclopropyl-C(O)— |
| 23 | 4-ethylphenyl | 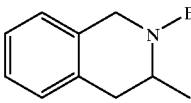 | —C(O)— |
| 24 | 4-ethylphenyl | | —C(O)— |
| 25 | trans-2-(4-chlorophenyl)ethenyl | 3-methoxyphenyl | —C(O)— |
| 26 | 4-chlorophenylethynyl | 3-methoxyphenyl | —C(O)— |
| 27 | phenylethynyl | 3-methoxyphenyl | —C(O)— |
| 28 | 4-ethylphenyl | phenyl | —C≡CC(O)— |
| 29 | 4-ethylphenyl | phenyl | —CH₂CH₂C(O)— |
| 30 | 3-tolyl | phenyl | —CH₂CH₂C(O)— |
| 31 | 4-cyanophenyl | phenyl | —CH₂CH₂C(O)— |
| 32 | 4-t-butylphenyl | 3-methoxyphenyl | —C(O)— |
| 33 | 4-ethylphenyl | 3-chlorophenyl | —C(O)— |
| 34 | 4-ethylphenyl | phenyl | —NHC(O)— |
| 35 | 4-ethylphenyl | phenyl | -trans-CHCHC(O)— |
| 36 | 4-ethylphenyl | phenylethynyl | —C(O)— |
| 37 | 4-ethylphenyl | 4-methoxyphenyl | —C≡CC(O)— |
| 38 | 4-n-propylphenyl | 2-methoxyphenyl | —C(O)— |
| 39 | 4-ethylphenyl | 4-ethylphenyl | —C(O)— |
| 40 | 4-isopropylphenyl | 4-ethylphenyl | —C(O)— |
| 41 | 4-n-propylphenyl | 4-ethylphenyl | —C(O)— |
| 42 | 4-ethylphenyl | 3-tolyl | —C(O)— |
| 43 | 4-biphenyl | 3,5-dimethoxyphenyl | —C(O)— |
| 44 | 4-n-propylphenyl | 3-tolyl | —C(O)— |
| 45 | 4-ethylphenyl | 3-ethoxyphenyl | —C(O)— |
| 46 | 4-isopropylphenyl | 3-ethoxyphenyl | —C(O)— |
| 47 | 4-n-propylphenyl | 3-ethoxyphenyl | —C(O)— |
| 48 | 2-naphthyl | 4-methoxyphenyl | —C(O)— |
| 49 | 4-isopropylphenyl | phenyl | -trans-CHCHC(O)— |
| 50 | 4-methoxyphenyl | phenyl | -trans-CHCHC(O)— |
| 51 | 3-tolyl | phenyl | -trans-CHCHC(O)— |
| 52 | phenyl | phenyl | -trans-CHCHC(O)— |
| 53 | trans-2-(4-chlorophenyl)ethenyl | phenyl | -trans-CHCHC(O)— |
| 54 | trans-2-(4-chlorophenyl)ethenyl | 4-tolyl | —C≡CC(O)— |
| 55 | 3-tolyl | 2,2-diphenethyl | —C(O)— |
| 56 | phenyl | 2,2-diphenethyl | —C(O)— |
| 57 | 4-methoxy-2,6-dimethylphenyl | 3-methoxyphenyl | —C(O)— |
| 58 | 4-ethylphenyl | phenyl-NH— | —CH₂C(O)— |
| 59 | 5-chloro-2-naphthyl | 4-methoxyphenyl | —C(O)— |
| 60 | 4-ethylphenyl | 4-trifluoromethoxyphenyl | —CH₂— |

TABLE 1A-continued

| Entry | R¹ | R² | —Y¹—X¹— |
|---|---|---|---|
| 61 | 3,4-dichlorophenyl | 3-trifluoromethoxyphenyl | —C(O)— |
| 62 | 3-tolyl | 3-trifluoromethoxyphenyl | —C(O)— |
| 63 | trans-β-styrenyl | 3-trifluoromethoxyphenyl | —C(O)— |
| 64 | 4-bromophenyl | 3-ethoxyphenyl | —C(O)— |
| 65 | 4-nitrophenyl | 3-methoxyphenyl | —C(O)— |
| 66 | 4-chlorophenylethynyl | 4-tolyl | —C≡CC(O)— |
| 67 | 4-chlorophenylethynyl | phenyl | —C≡CC(O)— |
| 68 | 4-chlorophenylethynyl | 4-tolyl | -trans-CHCHC(O)— |
| 69 | 4-chlorophenylethynyl | phenyl | -trans-CHCHC(O)— |
| 70 | benzyl | 3-methoxyphenyl | —C(O)— |
| 71 | benzyl | 4-ethylphenyl | —C(O)— |
| 72 | 4-nitrophenyl | 2-methoxyphenyl | —C(O)— |
| 73 | 4-n-propylphenyl | 4-methoxyphenyl | —C(O)— |
| 74 | 4-ethylphenyl | 3-acetylphenyl | —C(O)— |
| 75 | 4-acetylphenyl | 4-tolyl | —C(O)— |
| 76 | 4-tolyl | 3-methoxyphenyl | —C(O)— |
| 77 | 4-tolyl | 4-ethylphenyl | —C(O)— |
| 78 | 4-methoxyphenyl | 3-tolyl | —C(O)— |
| 79 | phenyl | 3-methoxyphenyl | —C(O)— |
| 80 | 4-methoxyphenyl | 3-methoxyphenyl | —C(O)— |
| 81 | 2-thienyl | 3-methoxyphenyl | —C(O)— |
| 82 | 4-ethylphenyl | phenyl | —CH₂C(O)— |
| 83 | 4-n-butylphenyl | phenyl | —CH₂C(O)— |
| 84 | 4-n-pentylphenyl | phenyl | —CH₂C(O)— |
| 85 | 4-n-propylphenyl | 4-nitrophenyl | —C(O)— |
| 86 | phenyl | 4-ethylphenyl | —C(O)— |
| 87 | phenyl | 3,4-dimethylphenyl | —C(O)— |
| 88 | 3-trifluoromethylphenyl | 3,4-dimethylphenyl | —C(O)— |
| 89 | 4-ethylphenyl | 3-tolyl | —C(O)— |
| 90 | 4-isopropylphenyl | 3-tolyl | —C(O)— |
| 91 | 4-methoxyphenyl | 3-tolyl | —C(O)— |
| 92 | 4-ethylphenyl | 4-fluorophenyl | —C(O)— |
| 93 | 4-isopropylphenyl | 4-fluorophenyl | —C(O)— |
| 94 | 4-n-propylphenyl | 4-fluorophenyl | —C(O)— |
| 95 | 3-tolyl | 4-ethylphenyl | —C(O)— |
| 96 | 3-nitrophenyl | 3,5-dimethoxyphenyl | —C(O)— |
| 97 | 3-tolyl | 3-tolyl | —C(O)— |
| 98 | 4-ethylphenyl | diphenethyl | —C(O)— |
| 99 | 4-isopropylphenyl | diphenethyl | —C(O)— |
| 100 | 4-n-propylphenyl | diphenethyl | —C(O)— |
| 101 | 4-methoxyphenyl | diphenethyl | —C(O)— |
| 102 | 3-tolyl | phenoxy | —CH₂C(O)— |
| 103 | 4-ethylphenyl | 2-thienyl | —C(O)— |
| 104 | 4-ethylphenyl | 4-dimethyl aminophenyl | —C(O)— |
| 105 | 4-isopropylphenyl | 2,2-dimethylethenyl | —C(O)— |
| 106 | 4-isopropylphenyl | 4-nitrophenyl | —C(O)— |
| 107 | 3-tolyl | 4-fluorophenyl | —C(O)— |
| 108 | 3-tolyl | 3-methoxyphenyl | —C(O)— |
| 109 | 2,3,6-trimethyl-4-methoxyphenyl | 3-methoxyphenyl | —C(O)— |
| 110 | 4-methoxy-2,3,6-trimethylphenyl | phenyl | —C(O)— |
| 111 | 2-phenethyl | 3-methoxyphenyl | —C(O)— |
| 112 | trans-2-phenylethenyl | 3-methoxyphenyl | —C(O)— |
| 113 | 4-n-propylphenyl | 3,5-dimethoxyphenyl | —C(O)— |
| 114 | 4-t-amylphenyl | 3-methoxyphenyl | —C(O)— |
| 115 | 4-isopropylphenyl | 4-methoxyphenyl | —CH₂C(O)— |
| 116 | 4-trifluoro methoxyphenyl | phenyl | —C(O)— |
| 117 | 4-trifluormethylphenyl | 3-tolyl | —C(O)— |
| 118 | 3-chlorophenyl | 3-methoxyphenyl | —C(O)— |

TABLE 1B

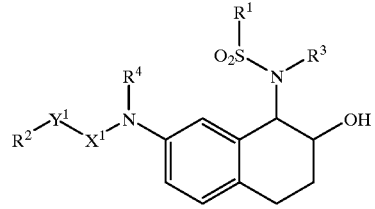

| Entry | R¹ | R² | R⁴ | R³ | —Y¹—X¹— |
|---|---|---|---|---|---|
| 119 | 4-ethylphenyl | 3-methoxyphenyl | benzyl | H | —C(O)— |
| 120 | 4-ethylphenyl | cyclopropyl | benzyl | H | —C(O)— |
| 121 | 4-ethylphenyl | 3-methoxyphenyl | butyl | H | —C(O)— |
| 122 | 4-ethylphenyl | 3-methoxyphenyl | 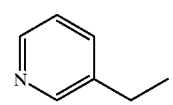 | H | —C(O)— |
| 123 | 4-ethylphenyl | cyclopropyl | 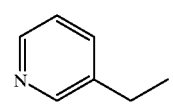 | H | —C(O)— |
| 124 | 4-methoxy-2,3,6-trimethylphenyl | 3-pyridine | H | H | —CH₂— |
| 125 | 4-ethylphenyl | cyclopropyl | 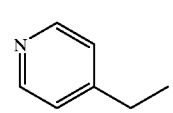 | H | —C(O)— |
| 126 | 4-trifluoromethoxy phenyl | 3-tolyl | 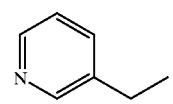 | H | —C(O)— |
| 127 | 4-ethylphenyl | 3-methoxyphenyl | 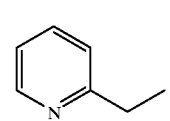 | H | —C(O)— |
| 128 | 4-ethylphenyl | 4-pyridine | H | H | —CH₂— |
| 129 | 4-methoxy-2,3,6-trimethylphenyl | 2-pyridine | H | H | —CH₂— |
| 130 | 4-ethylphenyl | 3-methoxyphenyl | ethyl | H | —C(O)— |
| 131 | 4-ethylphenyl | tert-butyl | H | 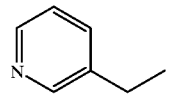 | —C(O)— |
| 132 | 4-ethylphenyl | 3-methoxyphenyl | H | 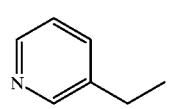 | —C(O)— |
| 133 | 4-ethylphenyl | 3-methoxyphenyl | H | benzyl | —C(O)— |
| 134 | 4-ethylphenyl | 3-methoxyphenyl | H | butyl | —C(O)— |

TABLE 1B-continued

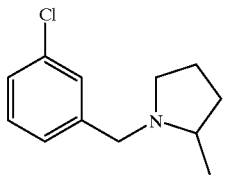

| Entry | R¹ | R² | R⁴ | R³ | —Y¹—X¹— |
|---|---|---|---|---|---|
| 135 | 4-ethylphenyl | 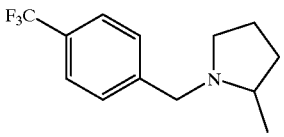 | H | H | —C(O)— |
| 136 | 4-ethylphenyl | 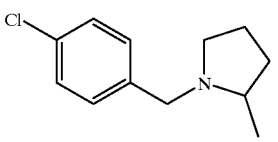 | H | H | —C(O)— |
| 137 | 4-ethylphenyl | 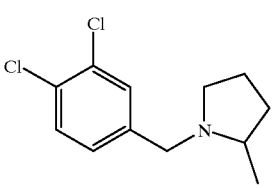 | H | H | —C(O)— |
| 138 | 4-ethylphenyl | 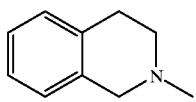 | H | H | —C(O)— |
| 139 | 4-ethylphenyl | phenyl-NH— | H | H | —CH₂C(O)— |
| 140 | 4-ethylphenyl | benzyl-NH— | H | H | —CH₂C(O)— |
| 141 | 4-ethylphenyl | 3,4-dimethoxy benzyl-NH— | H | H | —CH₂C(O)— |
| 142 | 4-ethylphenyl | 3,4-dimethyl phenyl-N(CH₃)— | H | H | —CH₂C(O)— |
| 143 | 4-ethylphenyl | 4-chlorobenzyl-N(CH₃)— | H | H | —CH₂C(O)— |
| 144 | 4-ethylphenyl | benzyl-N(CH₃)— | H | H | —CH₂C(O)— |
| 145 | 4-ethylphenyl | 4-methoxyphenyl-N(CH₃)— | H | H | —CH₂C(O)— |
| 146 | 4-ethylphenyl | 3,4-dimethoxy phenyl-N(CH₃)— | H | H | —CH₂C(O)— |
| 147 | 4-ethylphenyl | 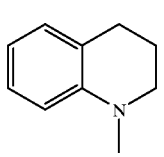 | H | H | —CH₂C(O)— |
| 148 | para-ethylphenyl |  | H | H | —CH₂C(O)— |

TABLE 1B-continued

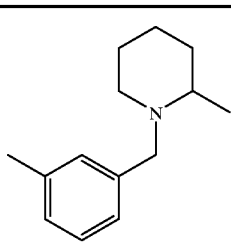

| Entry | R¹ | R² | R⁴ | R³ | —Y¹—X¹— |
|---|---|---|---|---|---|
| 149 | 4-ethylphenyl | 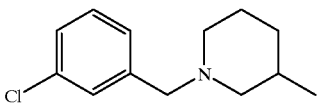 | H | H | —C(O)— |
| 150 | 4-ethylphenyl | | H | H | —C(O)— |
| 151 | 4-ethylphenyl | | H | H | —C(O)— |
| 152 | 4-ethylphenyl | | H | H | —C(O)— |
| 153 | 4-ethylphenyl | 4-methoxyphenyl | ethyl | methyl | —C(O)— |
| 154 | 4-ethylphenyl | 4-methoxyphenyl | 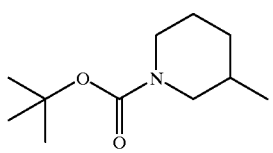 | methyl | —C(O)— |
| 155 | 4-ethylphenyl | 3-pyridine | ethyl | H | —CH₂— |
| 156 | 4-ethylphenyl | 3-methoxyphenyl | methyl | methyl | —CH₂— |
| 157 | 4-ethylphenyl | phenyl | methyl | H | —CH₂CH₂— |

TABLE 1C

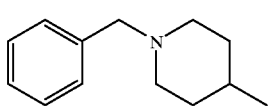

| Entry | R¹ | R² | R⁴ | R³ | —Y¹—X¹— |
|---|---|---|---|---|---|
| 158 | 4-ethylphenyl | 3-methoxyphenyl | H | H | —C(O)— |
| 159 | 4-ethylphenyl | 4-methoxyphenyl | H | H | —C(O)— |
| 160 | 4-ethylphenyl | t-butyl | H | H | —C(O)— |

TABLE 1C-continued

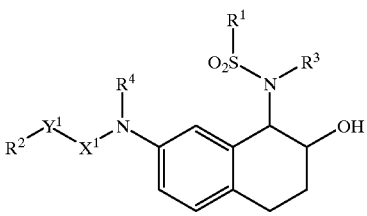

| Entry | R¹ | R² | R⁴ | R³ | —Y¹—X¹— |
|---|---|---|---|---|---|
| 161 | 4-ethylphenyl | 3-chlorophenyl | H | H | —C(O)— |
| 162 | 4-ethylphenyl | cyclopr0pane | 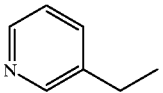 | H | —C(O)— |
| 163 | 4-ethylphenyl | methyl | 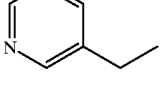 | H | —C(O)— |
| 164 | 4-ethylphenyl | t-butyl | 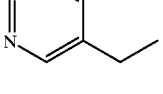 | H | —C(O)— |
| 165 | 4-ethylphenyl | 3-methoxyphenyl | 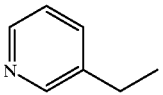 | H | —C(O)— |
| 166 | 4-ethylphenyl | 3-methoxyphenyl | H | 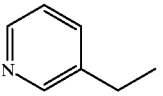 | —C(O)— |
| 167 | 4-ethylphenyl | cyclopropane | H | 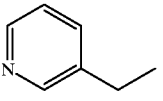 | —C(O)— |
| 168 | 4-ethylphenyl | t-butyl | H | 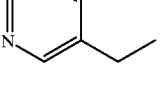 | —C(O)— |
| 169 | 4-ethylphenyl | H | 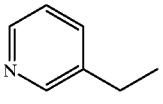 | H | —CH₂— |
| 170 | 4-methoxy-2,3,6-trimethylphenyl | 3-pyridyl | H | H | —CH₂— |
| 171 | 4-ethylphenyl | 4-pyridyl | H | H | —CH₂— |
| 172 | 4-ethylphenyl | 3-pyridyl | methyl | H | —CH₂— |
| 173 | 4-ethylphenyl | 4-CF₃O-phenyl | H | H | —CH₂— |
| 174 | 4-ethylphenyl | 3-pyridyl | H | 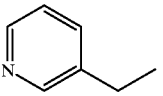 | —CH₂— |

TABLE 1C-continued

| Entry | R$^1$ | R$^2$ | R$^4$ | R$^3$ | —Y$^1$—X$^1$— |
|---|---|---|---|---|---|
| 175 | 4-ethylphenyl | 4-ethylphenyl | H | (3-pyridyl)ethyl | —CH$_2$— |

EXAMPLES

BioAssays $^{86}$Rb Efflux Assays

Cells stably transfected with cDNA for human Kv1.5 (in pcDNA3 vector) were grown as confluent monolayers in 96 well tissue culture plates in MEM alpha with 10% heat inactivated fetal bovine serum and 400 μg/ml G418. Cells were incubated overnight in growth media containing 1 μCi/ml $^{86}$Rb to permit intracellular uptake of the isotope. At the end of the incubation period, the $^{86}$Rb solution was aspirated and the cells washed three times with Earls Balanced Salt Solution (EBSS) which contained (in mM) 132 NaCl 5.4 KCl, 1.8 CaCl$_2$, 0.8 mM MgCl$_2$ 10 mM HEPES and 5 mM glucose. The cells were then preincubated for 10 minutes at room temperature in 100 μl/well of EBSS or EBSS containing test compounds. At the end of this period the wells were aspirated and to each well was then added 100 μl of a modified EBSS solution containing 70 mM KCl (NaCl replaced by KCl) and the compound to be tested. The high KCl concentration was utilized to depolarize the cells to membrane potentials that would activate Kv1.5 channels. After a 1 minute incubation in 70 mM KCl EBSS plus test compound, the solution was removed and placed into the appropriate well of a 96 well counting plate for analysis. Finally 100 μl of 0.1% sodium docecyl sulfate in EBSS was added to each well to lyse the cells. The lysate was taken for analysis to determine final cell content of $^{86}$Rb. Samples were counted in a Wallac Microbeta liquid scintillation counter by Cerenkov emission. Efflux was expressed as a percentage of the initial cell content of $^{86}$Rb.

The testing results of selective compounds from Tables 1A–C using this assay are reported in Table 2 (flux) as the potency for inhibition of $^{86}$Rb efflux through Kv1.5 potassium channels expressed in CHO cells by compounds of the invention.

Electrophysiological Studies

Electrophysiological recordings of potassium currents in Chinese hamster ovary cells stably expressing the gene construct for the Kv1.5 potassium channel subunit were performed using the whole cell configuration of the patch clamp technique (Hamill et al., *Pflugers Archiv* 391:85, 1981). Cell lines expressing Kv1.5 were prepared using standard techniques known to those skilled in the art. Cells were plated on glass coverslips at a density of 2×10$^4$ cells/coverslip and used within 24–48 hours. Solutions used for electrophysiological recordings were as follows. Extracellular bathing solutions contained (in mM) 132 NaCl, 5.4 KCl, 1.8 CaCl$_2$, 0.8 MgCl$_2$, 10 HEPES, 5 glucose at pH 7.3. Electrode pipette solutions for measuring Kv1.5 contain (in mM) 100 KCl 5 NaCl, 2 MgCl$_2$, 5 mM EGTA, 10 mM HEPES and 5 glucose at pH 7.4, 295 mOsm. The coverslips were placed in a small chamber (volume ~200 μl) on the mechanical stage of an inverted microscope and perfused (2 ml/min) with extracellular recording solution. Drug was applied using a series of narrow-bore glass capillary tubes (inner diameter ~100 μm) positioned approximately 200 μm from the cell.

The testing results of selective compounds from Tables 1A–C using this assay are reported in Table 2 as the potency for inhibition of Kv1.5 potassium currents by compounds of the invention

TABLE 2

| Entry # | IC$_{50}$ (μM) (EP) | IC$_{50}$ (μM) (flux) |
|---|---|---|
| 1 | 0.25 | 6.8 |
| 13 | 0.4 | >50 |
| 19 | 0.05 | 2.9 |
| 24 | 0.6 | 5.9 |
| 28 | 0.09 | 5.9 |
| 40 | ND | 9 |
| 60 | 0.5 | >50 |
| 70 | 2.1 | 29 |
| 85 | ND | 46 |
| 97 | ND | 39 |
| 103 | ND | 20 |
| 110 | ND | 12 |
| 123 | 0.1 | ND |
| 132 | 0.5 | ND |
| 135 | 0.1 | ND |
| 158 | 0.6 | ND |
| 162 | 0.2 | ND |

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications based on the above disclosure for making and using the compounds of the invention.

In the forgoing specification, the following abbreviations are used:

| Designation | Reagent or Fragment |
|---|---|
| m-CPBA | meta-chloroperoxybenzoic acid |
| THF | tetrahydrofuran |
| TLC | Thin Layer Chromatography |
| DMF | dimethylformamide |
| DMAP | para-dimethylaminopyridine |
| Me | methyl |
| Et | ethyl |
| EtOH | ethanol |
| MeOH | methanol |
| EtOAc | ethyl acetate |
| TsOH.H$_2$O | para-toluenesulfonic acid.water |
| NEt$_3$ | triethylamine |
| DMSO | dimethylsulfoxide |
| n-Pr | n-propyl |
| NMR | nuclear magnetic resonance |
| MHz | megahertz |
| Hz | hertz |
| CDCl$_3$ | chloroform-d |
| UV | ultra-violet |
| R$_f$ | retention factor |
| cat. | Catalytic |

We claim:

1. A compound of formula (I) or a pharmaceutically acceptable salt, ester, amide, complex, chelate, hydrate, stereoisomer, crystalline, or amorphous foam, metabolite, metabolic, precursor or prodrug thereof:

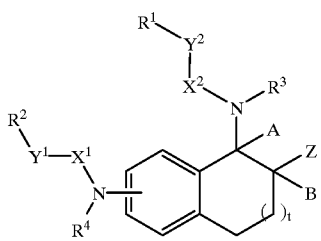

(I)

wherein t is 1, or 2;

A and B are each H, or taken together form a bond between the substituted carbons;

$R^1$ is H, alkyl, or is selected from the group consisting of an optionally substituted aryl, an optionally substituted heteroaryl, an optionally substituted heterocyclyl and an optionally substituted carbocycloalkyl with the proviso that when $R^1$ is an optionally substituted aryl, then $R^1$ is not a dialkoxyphenyl;

$Y^2$ is (CH$_2$)$_q$, (CH$_2$)$_w$O, HC=CH, ethynyl or NH, w is 0, 1, or 2 and q is 0, 1, or 2, with the proviso that if $Y^2$ is (CH$_2$)$_q$ and q=0, then $R^1$ cannot be H;

$X^2$ is C=O, C=S, or SO$_2$; with the proviso that is $Y^2$ is (CH$_2$)$_w$O, then $X^2$ is not SO$_2$;

$R^3$ is H, alkyl, an optionally substituted aryl, an optionally substituted aralkyl, an optionally substituted heteroaryl, an optionally substituted heteroaralkyl; an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC(O)(aryl), alkylene-NHC(O)(heterocyclyl), alkylene-NHC(O)-(heteroaralkyl), alkylene-C(O)(alkyl), alkylene-C(O)(alkyl), OR$^{14}$, SR$^{14}$ or NR$^{15}$R$^{16}$; where $R^{14}$ is selected from the group consisting of H, (CH$_2$)$_m$—R$^8$, or C(O)—(CH$_2$)$_r$—R$^8$; m is 1, 2, 3, or 4; r is 0, 1, 2, or 3; $R^8$ is CH$_2$N(R$^9$)$_3$L, or CO$_2$R$^9$; each $R^9$ is independently selected from H, or alkyl; L is a counter ion; $R^{15}$ is H, or alkyl; and $R^{16}$ is H, alkyl or CO$_2$R$^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, R$^a$—O—, and R$^b$R$^c$—N—; where R$^a$ and R$^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; R$^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or R$^b$ and R$^c$ along with the nitrogen to which they are attached form a heterocyclyl;

$Y^1$ is (CH$_2$)$_p$, CHR$^{17}$(CH$_2$)$_o$, HC=CH, or ethynyl; where R$^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1, or 2;

$X^1$ is C=O, C=S, SO$_2$ or (CH$_2$)$_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that if $Y^1$ is (CH$_2$)$_p$, p is 0 and $X^1$ is not (CH$_2$)$_n$, then $R^2$ is not H, (ii) that if $R^2$ is R$^a$—O and $Y^1$ is (CH$_2$)$_p$ with p=0, then $X^1$ is not SO$_2$ and (iii) if Z is not H, OR$^{14}$, SR$^{14}$ or NR$^{15}$R$^{16}$, then $X^2$ must be SO$_2$.

2. The compound of claim 1 wherein A and B are each H and the formula (I) has a stereochemical configuration of substituents in accordance with the following formula (Ia):

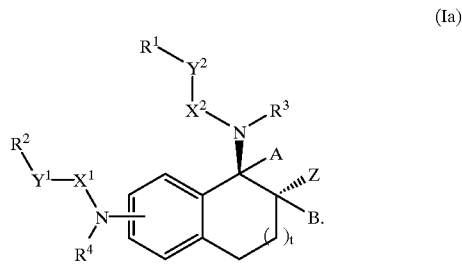

(Ia)

3. A compound of formula (II) or a pharmaceutically acceptable salt, ester, amide, complex, chelate, hydrate, stereoisomer, crystalline or amorphous form, metabolite, metabolic precursor or prodrug thereof:

(II)

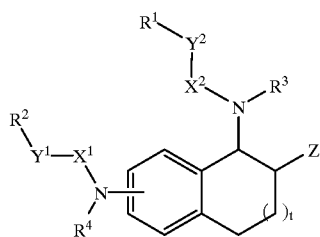

(I)

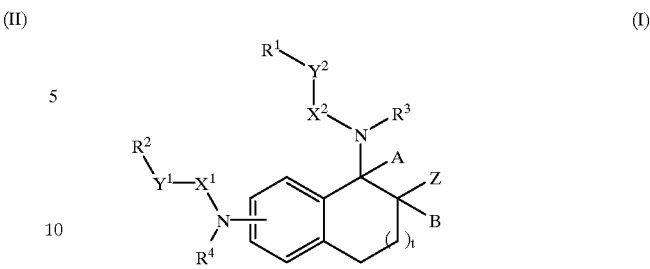

wherein t is 1, or 2;

R$^1$ is H, alkyl, or is selected from the group consisting of an optionally substituted aryl, an optionally substituted heteroaryl, an optionally substituted heterocyclyl and an optionally substituted carbocycloalkyl with the proviso that when R$^1$ is an optionally substituted aryl, then R$^1$ is not a dialkoxyphenyl;

Y$^2$ is (CH$_2$)$_q$(CH$_2$)$_w$O, HC=CH, ethynyl or NH w is 0, 1, or 2 and q is 0, 1, or 2, with the proviso that if Y$^2$ is (CH$_2$)$_q$ and q=0, then R$^1$ cannot be H;

X$^2$ is C=O, C=S, or SO$_2$; with the proviso that if Y$^2$ is (CH$_2$)$_w$O then X$^2$ is not SO$_2$;

R$^3$ is H, alkyl, an optionally substituted aryl, or an optionally substituted heteroaryl;

Z is H, OR$^{14}$, SR$^{14}$ or NR$^{15}$R$^{16}$; where R$^{14}$ is selected from the group consisting of H, (CH$_2$)$_m$—R$^8$, or C(O)—(CH$_2$)$_r$—R$^8$; m is 1, 2, 3, or 4; r is 0, 1, 2, or 3; R$^8$ is CH$_2$N(R$^9$)$_2$, CH$_2$N(R$^9$)$_3$L, or CO$_2$R$^9$; each R$^9$ is independently selected from H, or alkyl; L is a counter ion; R$^{15}$ is H, or alkyl; and R$^{16}$ is H, alkyl or CO$_2$R$^{10}$ and R$^{10}$ is H, or alkyl;

R$^2$ is selected from the group consisting of H, alkyl, an optionally substituted aryl, an optionally substituted heteroaryl, an optionally substituted heterocyclyl, an optionally substituted carbocycloalkyl, R$^a$—O—, and R$^b$R$^c$—N—; where R$^a$ and R$^b$ are independently selected from the group consisting of alkyl, an optionally substituted aryl, an optionally substituted heteroaryl, an optionally substituted heterocyclyl and an optionally substituted carbocycloalkyl; R$^c$ is selected from the group consisting of H, alkyl, an optionally substituted aryl, an optionally substituted heteroaryl, an optionally substituted heterocyclyl and an optionally substituted carbocycloalkyl;

Y$^1$ is (CH$_2$)$_p$, CHR$^{17}$(CH$_2$)$_o$, HC=CH, or ethynyl; where R$^{17}$ is alkyl or is selected from the group consisting of an optionally substituted aryl, an optionally substituted heteroaryl, an optionally substituted heterocyclyl and an optionally substituted carbocycloalkyl; p is 0, 1, 2, or 3; and o is 0, 1, or 2;

X$^1$ is C=O, C=S, SO$_2$ or (CH$_2$)$_n$; where n is 0, 1, or 2;

R$^4$ is H, alkyl, an optionally substituted aryl, or an optionally substituted heteroaryl; and with the provisos (i) that if Y$^1$ is (CH$_2$)$_p$, p is 0 and X$^1$ is not (CH$_2$)$_n$, then R$^2$ is not H, and (ii) that if R$^2$ is R$^a$—O— and Y$^1$ is (CH$_2$)$_p$ with p=0, then X$^1$ is not SO$_2$.

4. A compound of formula (I) or a pharmaceutically acceptable salt, ester, amide, complex, chelate, hydrate, stereoisomer, crystalline or amorphous form, metabolite, metabolic precursor or prodrug thereof:

wherein t is 1, or 2;

A and B are each H, or taken together form a bond between the substituted carbons;

R$^1$ is H, alkyl, or is selected from the group consisting of an optionally substituted aryl, an optionally substituted heteroaryl, an optionally substituted heterocyclyl and an optionally substituted carbocycloalkyl with the proviso that when R$^1$ is an optionally substituted aryl, then R$^1$ is not a dialkoxyphenyl;

Y$^2$ is (CH$_2$)$_q$, (CH$_2$)$_w$O, HC=CH ethynyl or NH, w is 0, 1, or 2 and q is 0, 1, or 2, with the proviso that if Y$^2$ is (CH$_2$)$_q$ and q=0, then R$^1$ cannot be H;

X$^2$ is C=O, C=S, or SO$_2$; with the proviso that if Y$^2$ is (CH$_2$)$_w$O, then X$^2$ is not SO$_2$;

R$^3$ is H, alkyl, an optionally substituted aryl, an optionally substituted aralkyl, an optionally substituted heteroaryl, an optionally substituted heteroaralkyl; an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkyleneheterocyclyl), alkylene-NHC(O)-(heteroaralkyl), alkylene-C(O)(alkyl), alkylene-C(O)O(alkyl), OR$^{14}$, SR$^{14}$ or NR$^{15}$R$^{16}$; where R$^{14}$ is selected from the group consisting of H, (CH$_2$)$_m$—R$^8$, or C(O)—CH$_2$)$_r$—R$^8$; m is 1, 2, 3, or 4; r is 0, 1, 2, or 3; R$^8$ is CH$_2$N(R$^9$)$_2$, CH$_2$N(R$^9$)$_3$L, or CO$_2$R$^9$; each R$^9$ is independently selected from H, or alkyl; L is a counter ion; R$^{15}$ is H, or alkyl; and R$^{16}$ is H, alkyl or CO$_2$R$^{10}$ and R$^{10}$ is H, or alkyl;

R$^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, R$^a$—O—, and R$^b$R$^c$—N—; where R$^a$ and R$^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; R$^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or R$^b$ and R$^c$ along with the nitrogen to which they are attached form a heterocyclyl;

Y$^1$ is (CH$_2$)$_p$, CHR$^{17}$(CH$_2$)$_o$, HC=CH, or ethynyl; where R$^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, $SO_2$, or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with provisos (i) that if $Y^1$ is $(CH_2)_p$, p is 0 and $X^1$ is not $(CH_2)_n$, then $R^2$ is not H, (ii) that if $R^2$ is $R^a$—O and $Y^1$ is $(CH_2)_p$ with p=0, then $X^1$ is not $SO_2$ and (iii) if Z is not H, $OR^{14}$, $SR^{14}$ or $NR^{15}R^{16}$, then $X^2$ must be $SO_2$.

5. The compound of claim 4 wherein A and B are each H and the formula (I) has a stereochemical configuration of substituents in accordance with the following formula (Ia):

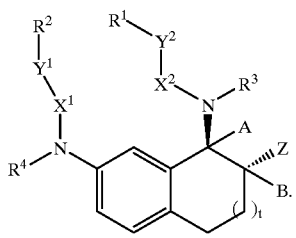

(Ia)

6. The compound of claim 1 or a pharmaceutically acceptable salt, ester, amide, complex, chelate, hydrate, stereoisomer, crystalline or amorphous form, metabolite, metabolic precursor or prodrug thereof, wherein A and B are each H;

$Y^2$ is $(CH_2)_q$, HC=CH, or ethynyl and q is 0, 1 or 2;

$X^2$ is $SO_2$;

$R^1$ is selected from the group of an optionally substituted aryl and an optionally substituted heteroaryl;

$X^1$ is C=O, C=S, or $(CH_2)_n$; wherein n is 0, 1, or 2; and

Z is H or $OR^{14}$.

7. The compound of claim 1 or a pharmaceutically acceptable salt, ester, amide, complex, chelate, hydrate, stereoisomer, crystalline or amorphous form, metabolite, metabolic precursor or prodrug thereof, wherein A and B are each H;

$Y^2$ is $(CH_2)_q$ and q is 0, 1, or 2;

$X^2$ is $SO_2$;

$R^1$ is H or an optionally substituted aryl selected from the group of phenyl and naphthyl;

$X^1$ is C=O, or $(CH_2)_n$; where n is 0, 1, or 2; and $Y^1$ is $(CH_2)_p$, CH=CH, or ethynyl where p is 0, 1, 2 or 3.

8. The compound of claim 4 or a pharmaceutically acceptable salt, ester, amide, complex, chelate, hydrate, stereoisomer, crystalline or amorphous form, metabolite, metabolic precursor or prodrug thereof, wherein t is 1;

A and B are each H;

$Y^2$ is $(CH_2)_q$ and q is 0;

$X^2$ is $SO_2$;

$R^1$ is an optionally substituted aryl selected from the group of phenyl and naphthyl;

$X^1$ is C=O, or $(CH_2)_n$; where n is 0, 1, or 2; and

Z is H, or OH; and $Y^1$ is CH=CH, ethynyl or $(CH_2)_p$, where p is 0, 1, 2 or 3.

9. The compound of claim 8 or a pharmaceutically acceptable salt, ester, amide, complex, chelate, hydrate, stereoisomer, crystalline or amorphous form, metabolite, metabolic precursor or prodrug thereof, wherein $R^3$ is H.

10. The compound of claim 9 wherein $R^1$ is an optionally substituted phenyl.

11. A pharmaceutical composition comprising a compound of claim 1 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

12. A pharmaceutical composition comprising a compound of claim 2 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

13. A pharmaceutical composition comprising a compound of claim 3 or its pharmaceutical acceptable salt, ester, amide, complex, chelate, hydrate, stereoisomer, crystalline or amorphous form, metabolite, metabolic precursor or prodrug and a pharmaceutically acceptable diluent or carrier.

14. A pharmaceutical composition comprising a compound of claim 4 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

15. A pharmaceutical composition comprising a compound of claim 5 or a pharmaceutically acceptable salt, ester, amide, complex, chelate, hydrate, stereoisomer, crystalline or amorphous form, metabolite, metabolic precursor or prodrug thereof and a pharmaceutically acceptable diluent or carrier.

16. A pharmaceutical composition comprising a compound of claim 6 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

17. A pharmaceutical composition comprising a compound of claim 7 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

18. A pharmaceutical composition comprising a compound of claim 8 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

19. A pharmaceutical composition comprising a compound of claim 9 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

20. A pharmaceutical composition comprising a compound of claim 10 or its pharmaceutically acceptable salt, ester, amide, complex, chelate, hydrate, stereoisomer, crystalline or amorphous form, metabolite, metabolic precursor or prodrug and a pharmaceutically acceptable diluent or carrier.

21. A method for inhibiting potassium transport across cellular membranes possessing potassium channels comprising exposing a cell membrane possessing said channels to the presence of a compound of formula (I) or a pharmaceutically acceptable salt, ester, amide, complex, chelate, hydrate, stereoisomer, crystalline or amorphous form, metabolite, metabolic precursor or prodrug thereof:

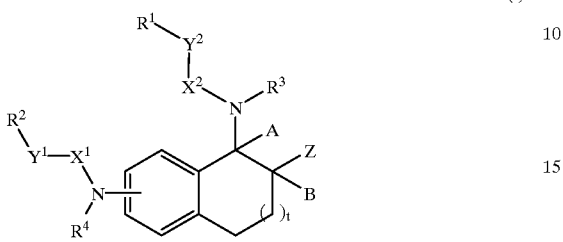

wherein t is 1, or 2;

A and B are each H, or taken together form a bond between the substituted carbons;

$R^1$ is H, alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$, $(CH_2)_wO$, HC=CH, ethynyl or NH, w is 0, 1, or 2 and q is 0, 1, or 2, with the proviso that if $Y^2$ is $(CH_2)_q$ and q=0, then $R^1$ cannot be H;

$X^2$ is C=O, C=S, or $SO_2$; with the proviso that if $Y^2$ is $(CH_2)_wO$, then $X^2$ is not $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC (O)(aryl), alkylene-NHC(O)(heterocyclyl), alkylene-NHC(O)(heteroaryl), alkylene-NHC(O)-(alkylene-heterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, $SO_2$ or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that if $Y^1$ is $(CH_2)_p$, p is 0 and $X^1$ is not $(CH_2)_n$, then $R^2$ is not H, (ii) that if $R^2$ is $R^a$—O and $Y^1$ is $(CH_2)_p$ with p=0, then $X^1$ is not $SO_2$, and (iii) if Z is not H, $OR^{14}$, $SR^{14}$ or $NR^{15}R^{16}$, then $X^2$ must be $SO_2$.

22. The method of claim 21 wherein the potassium channel is a voltage gated potassium channel.

23. The method of claim 22 wherein the potassium channel is selected from a potassium channel responsible for cardiac $I_{Kur}$ potassium current.

24. The method of claim 22 wherein the potassium channel is Kv1.5.

25. A method for inhibiting potassium transport across cellular membranes possessing potassium channels comprising exposing a cell membrane possessing said channels to the presence of a compound of formula (I) or a pharmaceutically acceptable salt, ester, amide, complex, chelate, hydrate, stereoisomer, crystalline or amorphous form, metabolite, metabolic precursor or prodrug:

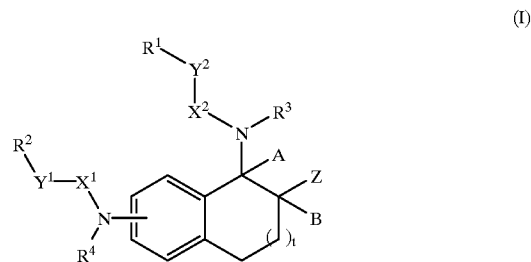

wherein t is 1, or 2;

A and B are each H;

$R^1$ is H, alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$, HC=CH, or ethynyl and q is 0, 1, or 2, with the proviso that when $Y^2$ is $(CH_2)_q$ and q=0, then $R^1$ cannot be H;

$X^2$ is $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC (O)(aryl), alkylene-NHC(O)(heterocyclyl), alkylene-NHC(O)(heteroaryl), alkylene-NHC(O)-(alkylene-heterocyclyl), alkylene-NHC(O)-heteroaryl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that when $Y^1$ is $(CH_2)_p$, p is 0 and $X^1$ is not $(CH_2)_n$, then $R^2$ is not H, and (ii) that if $R^2$ is $R^a$—O and $Y^1$ is $(CH_2)_p$ with p=0, then $X^1$ is not $SO_2$.

26. The method of claim 25 wherein the potassium channel is a voltage gated potassium channel.

27. The method of claim 26 wherein the potassium channel is selected from a potassium channel responsible for cardiac $I_{Kur}$ potassium current.

28. The method of claim 26 wherein the potassium channel is Kv1.5.

29. A method for inhibiting potassium transport across cellular membranes possessing potassium channels comprising exposing a cell membrane possessing said channels to the presence of a compound of formula (I) or a pharmaceutically acceptable salt, ester, amide, complex, chelate, hydrate, stereoisomer, crystalline or amorphous form, metabolite, metabolic precursor or prodrug:

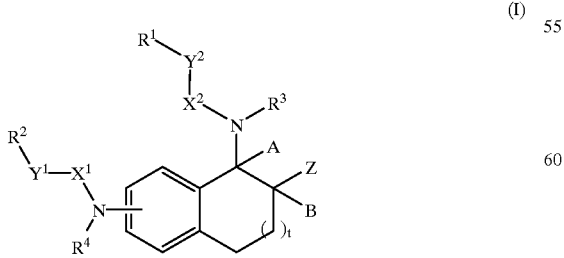

(I)

wherein t is 1, or 2;

A and B are each H;

$R^1$ is H, alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$ and q is 0, 1, or 2, with the proviso that when q=0, then $R^1$ cannot be H;

$X^2$ is $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkyleneheterocyclyl), alkylene (heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkyleneheterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the proviso that when $Y^1$ is $(CH_2)_p$ and p is 0, then $R^2$ is not H.

30. The method of claim 29 wherein the potassium channel is a voltage gated potassium channel.

31. The method of claim 30 wherein the potassium channel is selected from a potassium channel responsible for cardiac $I_{Kur}$ potassium current.

32. The method of claim 30 wherein the potassium channel is Kv1.5.

33. A method for inhibiting potassium transport across cellular membranes possessing potassium channels comprising exposing a cell membrane possessing said channels to the presence of a compound of formula (I) or a pharmaceutically acceptable salt, ester, amide, complex, chelate, hydrate, stereoisomer, crystalline or amorphous form, metabolite, metabolic precursor or prodrug thereof:

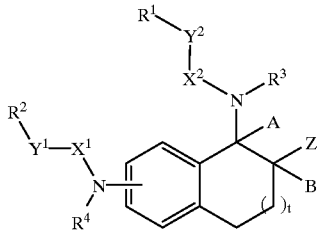

(I)

wherein t is 1;

A and B are each H;

$R^1$ is alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$ and q is 0;

$X^2$ is $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkylene-heterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or $C(O)$—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, or $(CH_2)_n$; where n is 0, 1, or 2;

$R^4$ is H alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the proviso that when $Y^1$ is $(CH_2)_p$ and p is 0, then $R^2$ is not H.

34. The method of claim 33 wherein the potassium channel is a voltage gated potassium channel.

35. The method of claim 34 wherein the potassium channel is selected from a potassium channel responsible for cardiac $I_{Kur}$ potassium current.

36. The method of claim 34 wherein the potassium channel is Kv1.5.

37. A method for treating cardiac arrhythmias which comprises administering to a patient in need thereof, a pharmaceutically effective amount of a compound of formula (I) or a pharmaceutically acceptable salt, ester, amide, complex, chelate, hydrate, stereoisomer, crystalline or amorphous form, metabolite, metabolic precursor or prodrug thereof:

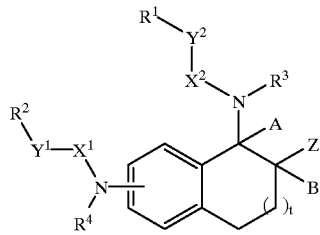

(I)

wherein t is 1, or 2;

A and B are each H, or taken together form a bond between the substituted carbons;

$R^1$ is H alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$, $(CH_2)_wO$, HC=CH, ethynyl or NH w is 0, 1, or 2 and q is 0, 1, or 2, with the proviso that if $Y^2$ is $(CH_2)_q$ and q=0, then $R^1$ cannot be H;

$X^2$ is C=O, C=S, or $SO_2$; with the proviso that if $Y^2$ is $(CH_2)_wO$, then $X^2$ is not $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkylene-heterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or $C(O)$—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^b R^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, $SO_2$ or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that if $Y^1$ is $(CH_2)_p$, p is 0 and $X^1$ is not $(CH_2)_n$, then $R^2$ is not H, (ii) that if $R^2$ is $R^a$—O and $Y^1$ is $(CH_2)_p$ with p=0, then $X^1$ is not $SO_2$ and (iii) if Z is not H, $OR^{14}$, $SR^{14}$ or $NR^{15}R^{16}$, then $X^2$ must be $SO_2$.

38. A method for treating cardiac arrhythmias which comprises administering to a patient in need thereof, a pharmaceutically effective amount of a compound of formula (II) or a pharmaceutically acceptable salt, ester, amide, complex, chelate, hydrate, stereoisomer, crystalline or amorphous form, metabolite, metabolic precursor or prodrug thereof:

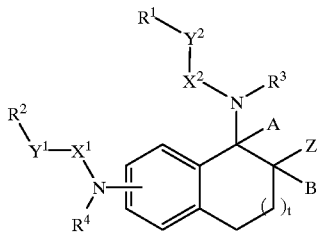

(I)

wherein t is 1, or 2;

A and B are each H;

$R^1$ is H, alkyl, or is selected from the group consisting of an optionally substituted aryl, an optionally substituted heteroaryl, an optionally substituted heterocyclyl and an optionally substituted carbocycloalkyl;

$Y^2$ is $(CH_2)_q$, HC=CH, or ethynyl and q is 0, 1, or 2, with the proviso that when $Y^2$ is $(CH_2)_q$ and q=0, then $R^1$ cannot be H;

$X^2$ is $SO_2$;

$R^3$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkenyl, alkylene(heterocyclyl), alkylene(heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkylene-heterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^b R^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that when $Y^1$ is $(CH_2)_p$, p is 0 and $X^1$ is not $(CH_2)_n$, then $R^2$ is not H, and (ii) that if $R^2$ is $R^a$—O and $Y^1$ is $(CH_2)_p$ with p=0, then $X^1$ is not $SO_2$.

39. A method for treating cardiac arrhythmias which comprises administering to a patient in need thereof, a pharmaceutically effective amount of a compound of formula (III) or a pharmaceutically acceptable salt, ester, amide, complex, chelate, hydrate, stereoisomer, crystalline or amorphous form, metabolite, metabolic precursor or prodrug thereof:

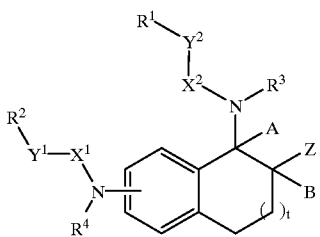

(I)

wherein t is 1, or 2;

A and B are each H;

R¹ is H, alkyl, or is selected from the group consisting of an optionally substituted aryl, an optionally substituted heteroaryl, an optionally substituted heterocyclyl and an optionally substituted carbocycloalkyl;

Y² is $(CH_2)_q$ and q is 0, 1, or 2, with the proviso that when q=0, then R¹ cannot be H;

X² is $SO_2$;

R³ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene(heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkyleneheterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—R⁸, or C(O)—$(CH_2)_r$—R⁸; m is 1, 2, 3, or 4; r is 0, 1, 2, or 3; R⁸ is $CH_2N(R^9)_2$, $CH_2N(R^9)_3L$, or $CO_2R^9$; each R⁹ is independently selected from H, or alkyl; L is a counter ion; $R^{15}$ is H, or alkyl; and $R^{16}$ is H, alkyl or $CO_2R^{10}$ and $R^{10}$ is H, or alkyl;

R² is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

Y¹ is $(CH_2)_p$, C=O, $(CH_2)_o$; HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

X¹ is C=O, or $(CH_2)_n$; where n is 0, 1, or 2;

R⁴ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the proviso that when Y¹ is $(CH_2)_p$ and p is 0, then R² is not H.

40. A method for treating cardiac arrhythmias which comprises administering to a patient in need thereof, a pharmaceutically effective amount of a compound of formula (IV) or a pharmaceutically acceptable salt, ester, amide, complex, chelate, hydrate, stereoisomer, crystalline or amorphous form, metabolite, metabolic precursor or prodrug thereof:

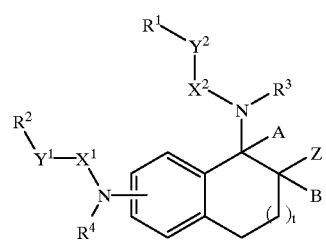

(I)

wherein t is 1;

A and B are each H;

R¹ is alkyl, or is selected from the group consisting of an optionally substituted aryl, an optionally substituted heteroaryl, an optionally substituted heterocyclyl and an optionally substituted carbocycloalkyl;

Y² is $(CH_2)_q$ and q is 0;

X² is $SO_2$;

R³ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino);

Z is H, alkyl, alkyenyl, alkylene(heterocyclyl), alkylene(heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkyleneheterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—R⁸, or C(O)—$(CH_2)_r$—R⁸; m is 1, 2, 3, or 4; r is 0, 1, 2, or 3; R⁸ is $CH_2N(R^9)_2$, $CH_2N(R^9)_3L$, or $CO_2R^9$; each R⁹ is independently selected from H, or alkyl; L is a counter ion; $R^{15}$ is H, or alkyl; and $R^{16}$ is H, alkyl or $CO_2R^{10}$ and $R^{10}$ is H, or alkyl;

R² is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, or $(CH_2)_n$; where n is 0, 1, or 2;

$R^4$ is H, alkyl an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the proviso that when $Y^1$ is $(CH_2)_p$ and p is 0, then $R^2$ is not H.

41. A compound of formula (I) or a pharmaceutically acceptable salt, ester, amide, complex, chelate, hydrate, stereoisomer, crystalline or amorphous form, metabolite, metabolic precursor or prodrug thereof:

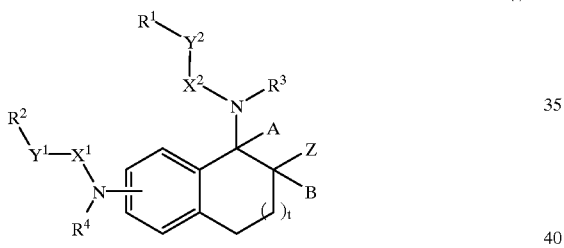

(I)

wherein t is 1, or 2;

A and B are each H or taken together form a bond between the substituted carbons;

$R^1$ is H, alkyl, or is selected from the group consisting of an optionally substituted aryl, an optionally substituted heteroaryl, an optionally substituted heterocyclyl and an optionally substituted carbocycloalkyl with the proviso that when $R^1$ is an optionally substituted aryl, then $R^1$ is not a dialkoxyphenyl;

$Y^2$ is $(CH_2)_q$, HC=CH, ethynyl or NH q is 0, 1, or 2, with the proviso that if $Y^2$ is $(CH_2)_q$ and q=0, then $R^1$ cannot be H;

$X^2$ is $SO_2$;

$R^3$ is H, alkyl, an optionally substituted aryl, an optionally substituted aralkyl, an optionally substituted heteroaryl, an optionally substituted heteroaralkyl; an optionally substituted heterocyclyl, an optionally substituted carbocycloalkyl, or an alkylene-(substituted amino);

Z is H, alkyl, alkyenyl, alkylene(heterocyclyl), alkylene (heteroaryl), alkylene-NHC(O)(alkyl), alkylene-NHC(O)(aryl), alkylene-NHC(O)(heterocyclyl), alkylene-NHC(O)(heteroaryl), alkylene-NHC(O)-(alkylene-heterocyclyl), alkylene-NHC(O)-(heteroaralkyl), alkylene-C(O)(alkyl), alkylene-C(O)O(alkyl), $OR^{14}$, $SR^{14}$ or $NR^{15}R^{16}$; where $R^{14}$ is selected from the group consisting of H, $(CH_2)_m$—$R^8$, or C(O)—$(CH_2)_r$—$R^8$; m is 1, 2, 3, or 4; r is 0, 1, 2, or 3; $R^8$ is $CH_2N(R^9)_2$, $CH_2N(R^9)_3L$, or $CO_2R^9$; each $R^9$ is independently selected from H, or alkyl; L is a counter ion; $R^{15}$ is H, or alkyl; and $R^{16}$ is H, alkyl or $CO_2R^{10}$ and $R^{10}$ is H, or alkyl;

$R^2$ is selected from the group consisting of H, alkyl, an optionally substituted aryl, an optionally substituted aralkyl, an optionally substituted heteroaryl, an optionally substituted heterocyclyl, an optionally substituted heteroaralkyl, an optionally substituted carbocycloalkyl, $R^a$—O—, and $R^bR^c$—N—; where $R^a$ and $R^b$ are independently selected from the group consisting of alkyl, an optionally substituted aryl, an optionally substituted aralkyl, an optionally substituted heteroaryl, an optionally substituted heterocyclyl, an optionally substituted heteroaralkyl, and an optionally substituted carbocycloalkyl; $R^c$ is selected from the group consisting of H, alkyl, an optimally substituted aryl, an optionally substituted aralkyl, an optionally substituted heteroaryl, an optionally substituted heterocyclyl, an optionally substituted heteroaralkyl, and an optionally substituted carbocycloalkyl; or $R^b$ and $R^c$ along with the nitrogen to which they are attached form a heterocyclyl;

$Y^1$ is $(CH_2)_p$, $CHR^{17}(CH_2)_o$, HC=CH, or ethynyl; where $R^{17}$ is alkyl or is selected from the group consisting of an optionally substituted aryl, an optionally substituted heteroaryl, an optionally substituted heterocyclyl and an optionally substituted carbocycloalkyl; p is 0, 1, 2 or 3; and o is 0, 1 or 2;

$X^1$ is C=O, C=S, $SO_2$ or $(CH_2)_n$; where n is 0, 1, or 2;

$R^4$ is H, alkyl, an optionally substituted aryl, an optionally substituted aralkyl, an optionally substituted heteroaryl, an optionally substituted heteroaralkyl; an optionally substituted heterocycle, an optionally substituted heterocyclyl, an optionally substituted carbocycloalkyl, or an alkylene-(substituted amino); and with the provisos (i) that if $Y^1$ is $(CH_2)_p$, p is 0 and $X^1$ is not $(CH_2)_n$, then $R^2$ is not H; and (ii) that if $R^2$ is $R^a$—O and $Y^1$ is $(CH_2)_p$ with p=0, then $X^1$ is not $SO_2$.

42. The compound of claim 8 having the following formula, or a pharmaceutically acceptable salt, ester, amide, complex, chelate, hydrate, stereoisomer, crystalline or amorphous form, metabolite, metabolic precursor or prodrug thereof:

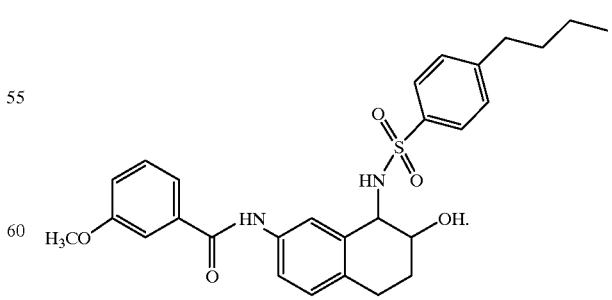

* * * * *